United States Patent [19]

Matsuda et al.

[11] Patent Number: 5,466,598
[45] Date of Patent: Nov. 14, 1995

[54] **DEACETYLCEPHALOSPORIN C ACETYLTRANSFERASE FROM *ACREMONIUM CHRYSOGENUM***

[75] Inventors: Akio Matsuda, Fuji; Kenji Matsuyama, Shiraoi, both of Japan

[73] Assignee: Asahi Kasei Kogyo Kabushiki Kaisha, Osaka, Japan

[21] Appl. No.: 178,606

[22] Filed: Jan. 7, 1994

Related U.S. Application Data

[63] Continuation of Ser. No. 661,615, Feb. 28, 1991, abandoned.

[30] Foreign Application Priority Data

Mar. 2, 1990 [JP] Japan ......................... 2-49434

[51] Int. Cl.⁶ .............................. C12N 1/14; C12N 9/10; C12N 15/54; C12P 35/06
[52] U.S. Cl. ..................... 435/254.11; 435/193; 435/49; 435/320.1; 435/256.4; 536/23.2
[58] Field of Search .............................. 536/23.2; 435/49, 435/69.1, 172.3, 193, 252.3, 254, 255.320.1, 254.11, 256.4

[56] References Cited

FOREIGN PATENT DOCUMENTS

| | | |
|---|---|---|
| 0238323 | 9/1987 | European Pat. Off. . |
| 0281391 | 7/1988 | European Pat. Off. . |
| 0376226 | 4/1990 | European Pat. Off. . |
| 437378 | 7/1991 | European Pat. Off. . |
| 9010074 | 7/1990 | WIPO . |

OTHER PUBLICATIONS

Scheidegger et al., Journal of Biotechnology, 3 (1985) 109–117.
Skatrud et al., Biotechnology, pp. 477–485, vol. 7 (1989).
Fujisawa et al., Agr. Biol. Chem. 39, 2043–2048 (1975).
Matsuda et al. (1992) Biochem Biophys Res. Comm. 182, 995–1001.
Samson et al. (1985) Nature 318, 191–194.
Davis et al. (1986) in "Basic Methods in Molecular Biology" Elsevier, New York, pp. 194–218.

*Primary Examiner*—Robert A. Wax
*Assistant Examiner*—Keith D. Hendricks
*Attorney, Agent, or Firm*—Birch, Stewart, Kolasch & Birch

[57] ABSTRACT

A DNA is disclosed, which comprises a gene coding for deacetylcephalosporin C acetyltransferase, i.e., an enzyme capable of catalyzing the final step of the biosynthesis of cephalosporin C. The gene may be either a cDNA or a genomic DNA. Also disclosed is a recombinant DNA comprising a vector having inserted therein at least a portion of the above-mentioned DNA, which recombinant DNA is in a form such that the portion is capable of expression in *Acremonium chrysogenum*. *Acremonium chrysogenum* transformed with the recombinant DNA can be advantageously used for efficiently preparing cephalosporin C.

11 Claims, 15 Drawing Sheets

```
                                        10         20         30
                               GAATTCCCTCACCTACAGCCACACGTCGCCCACC
    40         50         60         70         80         90
ATGTCGCCTCAGATCGCCAATCGCTTCGAGGCTTCGCTAGATGCCCAAGACATAGCCAGA
MetSerProGlnIleAlaAsnArgPheGluAlaSerLeuAspAlaGlnAspIleAlaArg 100        110        120        130        140        150
ATATCGCTCTTCACACTGGAATCTGGCGTCATCCTTCGCGATGTACCCGTGGCATACAAA
IleSerLeuPheThrLeuGluSerGlyValIleLeuArgAspValProValAlaTyrLys
                                                   ①
   160        170        180        190        200        210
TCGTGGGGTCGCATGAATGTCTCAAGGGATAACTGCGTCATCGTCTGCCACACCTTGACG
SerTrpGlyArgMetAsnValSerArgAspAsnCysValIleValCysHisThrLeuThr 220        230        240        250        260        270
AGCAGCGCCCATGTCACCTCGTGGTGGCCCACACTGTTTGGCCAAGGCAGGGCTTTCGAT
SerSerAlaHisValThrSerTrpTrpProThrLeuPheGlyGlnGlyArgAlaPheAsp 280        290        300        310        320        330
ACCTCTCGCTACTTCATCATCTGCCTAAATTATCTCGGGAGCCCCTTTGGGAGTGCTGGA
ThrSerArgTyrPheIleIleCysLeuAsnTyrLeuGlySerProPheGlySerAlaGly 340        350        360        370        380        390
CCATGTTCACCGGACCCCGATGCAGAAGGCCAGCGCCCGTACGGGGCCAAGTTTCCTCGC
ProCysSerProAspProAspAlaGluGlyGlnArgProTyrGlyAlaLysPheProArg 400        410        420        430        440        450
ACGACGATTCGAGATGATGTTCGTATTCATCGCCAGGTGCTCGACAGGTTAGGCGTCAGG
ThrThrIleArgAspAspValArgIleHisArgGlnValLeuAspArgLeuGlyValArg 460        470        480        490        500        510
CAAATTGCTGCCGTAGTCGGCGCATCCATGGGTGGAATGCACACTCTGGAATGGGCCTTC
GlnIleAlaAlaValValGlyAlaSerMetGlyGlyMetHisThrLeuGluTrpAlaPhe 520        530        540        550        560        570
TTTGGTCCCGAGTACGTGCGAAAGATTGTGCCCATCGCGACATCATGCCGTCAGAGCGGC
PheGlyProGluTyrValArgLysIleValProIleAlaThrSerCysArgGlnSerGly 580        590        600        610        620        630
TGGTGCGCAGCTTGGTTCGAGACACAGAGGCAGTGCATCTATGATGACCCCAAGTACCTG
TrpCysAlaAlaTrpPheGluThrGlnArgGlnCysIleTyrAspAspProLysTyrLeu 640        650        660        670        680        690
GACGGGGAGTACGACGTAGACGACCAGCCTGTCCGGGGGCTCGAAACAGCGCGCAAGATT
AspGlyGluTyrAspValAspAspGlnProValArgGlyLeuGluThrAlaArgLysIle 700        710        720        730        740        750
GCGAATCTCACGTACAAGAGCAAACCTGCGATGGACGAGCGCTTCCATATGGCTCCAGGA
AlaAsnLeuThrTyrLysSerLysProAlaMetAspGluArgPheHisMetAlaProGly
```

FIG. 2 (b)

```
         760       770       780       790       800       810
GTCCAAGCCGGCCGGAATATCAGCAGCCAGGATGCGAAGAAGGAAATCAACGGCACAGAC
ValGlnAlaGlyArgAsnIleSerSerGlnAspAlaLysLysGluIleAsnGlyThrAsp 820       830       840       850       860       870
AGCGGCAACAGCCACCGTGCTGGCCAGCCCATTGAAGCCGTATCTTCCTATCTCCGGTAC
SerGlyAsnSerHisArgAlaGlyGlnProIleGluAlaValSerSerTyrLeuArgTyr 880       890       900       910       920       930
CAGGCCCAGAAGTTTGCCGCGAGCTTCGACGCCAACTGCTACATCGCCATGACACTCAAG
GlnAlaGlnLysPheAlaAlaSerPheAspAlaAsnCysTyrIleAlaMetThrLeuLys
                                                          ②
         940       950       960       970       980       990
TTCGACACCCACGACATCAGCAGAGGCCGGGCAGGATCAATCCCGGAGGCTCTGGCAATG
PheAspThrHisAspIleSerArgGlyArgAlaGlySerIleProGluAlaLeuAlaMet 1000      1010      1020      1030      1040      1050
ATTACACAACCAGCGTTGATCATTTGCGCCAGGTCAGACGGTCTGTACTCGTTTGACGAG
IleThrGlnProAlaLeuIleIleCysAlaArgSerAspGlyLeuTyrSerPheAspGlu 1060      1070      1080      1090      1100      1110
CACGTTGAGATGGGGCGCAGTATCCCAAACAGTCGTCTTTGCGTGGTGGACACGAATGAG
HisValGluMetGlyArgSerIleProAsnSerArgLeuCysValValAspThrAsnGlu 1120      1130      1140      1150      1160      1170
GGTCATGACTTCTTTGTAATGGAAGCGGACAAGGTTAATGATGCCGTCAGAGGATTCCTC
GlyHisAspPhePheValMetGluAlaAspLysValAsnAspAlaValArgGlyPheLeu 1180      1190      1200      1210      1220      1230
GATCAGTCATTAATGTGAGGCTATGGAGGTGTCAGAAAAAAAAAAAAAAAAAAAAAAAA
AspGlnSerLeuMet***

1240
AAGGAATTC
```

NUCLEOTIDE SEQUENCE-DETERMINED REGION

FIG. 4(a)

```
  1 AGATCTTGCTAATACGAGTCGGAGAGTTACTATTCCGGGCTTATGCGGACGGGCC

56 GCCGCCGTCGATGCCGGCCAAGGCTTGTCGTGCATGATAGATGCTGCCGTCGGCC

111 CAAGTGGCCCGTCTAAAGCCGGACCCCTTTCCCCCGAGTCTCTCCCCGATCCCGC

166 ACGGGGCCGTCACTTTCGCTGCCCTCGCTCCTTGTCATAACCTACCTATATTCTC

221 ATCCCGGCAAATGCTGCGGGATAGCCTCACCTACAGCCACACGTCGCCCACCATG
                                                       Met

276 TCGCCTCAGATCGCCAATCGCTTCGAGGCTTCGCTAGATGCCCAAGACATAGCC
    SerProGlnIleAlaAsnArgPheGluAlaSerLeuAspAlaGlnAspIleAla

330 AGAATATCGCTCTTCACACTGGAATCTGGCGTCATCCTTCGCGATGTACCCGTG
    ArgIleSerLeuPheThrLeuGluSerGlyValIleLeuArgAspValProVal

384 GCATACAAATCGTGGGGTCGCATGAATGTCTCAAGGGATAACTGCGTCATCGTC
    AlaTyrLysSerTrpGlyArgMetAsnValSerArgAspAsnCysValIleVal

438 TGCCACACCTTGACGAGCAGCGCCCATGTCACCTCGTGGTGGCCCACACTGTTT
    CysHisThrLeuThrSerSerAlaHisValThrSerTrpTrpProThrLeuPhe

492 GGCCAAGGCAGGGCTTTCGATACCTCTCGCTACTTCATCATCTGCCTAAATTAT
    GlyGlnGlyArgAlaPheAspThrSerArgTyrPheIleIleCysLeuAsnTyr

546 CTCGGGAGCCCCTTTGGGAGTGCTGGACCATGTTCACCGGACCCCGATGCAGAA
    LeuGlySerProPheGlySerAlaGlyProCysSerProAspProAspAlaGlu

600 GGCCAGCGCCCGTACGGGGCCAAGTTTCCTCGCACGACGATTCGAGATGATGTT
    GlyGlnArgProTyrGlyAlaLysPheProArgThrThrIleArgAspAspVal

654 CG/GTAGGTAAGCGCACCGATCCAGCTTGTCTCAATATCGAGTGGTCAGGACAAT
    Arg

708 CCAGGCTAAGCTTTCCGTGTCCAAAAG/TATTCATCGCCAGGTGCTCGACAGG
                                 IleHisArgGlnValLeuAspArg

760 TTAGGCGTCAGGCAAATTGCTGCCGTAGTCGGCGCATCCATGGGTGGAATGCAC
    LeuGlyValArgGlnIleAlaAlaValValGlyAlaSerMetGlyGlyMetHis

814 ACTCTGGAATGGGCCTTCTTTGGTCCCGAGTACGTGCGAAAGATTGTGCCCATC
    ThrLeuGluTrpAlaPhePheGlyProGluTyrValArgLysIleValProIle

868 GCGACATCATGCCGTCAGAGCGGCTGGTGCGCAGCTTGGTTCGAGACACAGAGG
    AlaThrSerCysArgGlnSerGlyTrpCysAlaAlaTrpPheGluThrGlnArg

922 CAGTGCATCTATGATGACCCCAAGTACCTGGACGGGGAGTACGACGTAGACGAC
    GlnCysIleTyrAspAspProLysTyrLeuAspGlyGluTyrAspValAspAsp

976 CAGCCTGTCCGGGGGCTCGAAACAGCGCGCAAGATTGCGAATCTCACGTACAAG
    GlnProValArgGlyLeuGluThrAlaArgLysIleAlaAsnLeuThrTyrLys
```

FIG.4(b)

```
1030 AGCAAACCTGCGATGGACGAGCGCTTCCATATGGCTCCAGGAGTCCAAGCCG/
     SerLysProAlaMetAspGluArgPheHisMetAlaProGlyValGlnAlaGly

1082 GTGAGTTTATAGATGCCTTGCCGTCGGTCGATGCTCAGAGCTAATCAGACCGAA

1136 CCCGCTGCTAG/ GCCGGAATATCAGCAGCCAGGATGCGAAGAAGGAAATCAAC
                 ArgAsnIleSerSerGlnAspAlaLysLysGluIleAsn

1188 GGCACAGACAGCGGCAACAGCCACCGTGCTGGCCAGCCCATTGAAGCCGTATCT
     GlyThrAspSerGlyAsnSerHisArgAlaGlyGlnProIleGluAlaValSer

1242 TCCTATCTCCGGTACCAGGCCCAGAAGTTTGCCGCGAGCTTCGACGCCAACTGC
     SerTyrLeuArgTyrGlnAlaGlnLysPheAlaAlaSerPheAspAlaAsnCys

1296 TACATCGCCATGACACTCAAGTTCGACACCCACGACATCAGCAGAGGCCGGGCA
     TyrIleAlaMetThrLeuLysPheAspThrHisAspIleSerArgGlyArgAla

1350 GGATCAATCCCGGAGGCTCTGGCAATGATTACACAACCAGCGTTGATCATTTGC
     GlySerIleProGluAlaLeuAlaMetIleThrGlnProAlaLeuIleIleCys

1404 GCCAGGTCAGACGGTCTGTACTCGTTTGACGAGCACGTTGAGATGGGGCGCAGT
     AlaArgSerAspGlyLeuTyrSerPheAspGluHisValGluMetGlyArgSer

1458 ATCCCAAACAGTCGTCTTTGCGTGGTGGACACGAATGAGGGTCATGACTTCTTT
     IleProAsnSerArgLeuCysValValAspThrAsnGluGlyHisAspPhePhe

1512 GTAATGGAAGCGGACAAGGTTAATGATGCCGTCAGAGGATTCCTCGATCAGTCA
     ValMetGluAlaAspLysValAsnAspAlaValArgGlyPheLeuAspGlnSer

1566 TTAATGTGAGGCTATGGAGGTGTCAGCCTGCCGGTGCGCGTACTTGCCAGGGTGA
     LeuMet*

1621 TCGATGTACTCTCAGATAGTCTCCATGTGAGTATGGATTTCGCTGTTTCCGCTCG

1676 GATATAGGCACTCTCAGGCCATCTCGCAGTAGGTATCAGAACAGCAGCTGAGGCC

1731 T
```

DEACETYLCEPHALOSPORIN C ACETYLTRANSFERASE FROM *ACREMONIUM CHRYSOGENUM*

This application is a continuation, of application Ser. No. 07/661,615 filed on Feb. 28, 1991, now abandoned.

BACKGROUND OF THE INVENTION

1. Field of the Invention

The present invention relates to an acetyltransferase gene-containing DNA. More particularly, the present invention is concerned with a DNA comprising a gene coding for deacetylcephalosporin C acetyltransferase which is an enzyme capable of catalyzing the final step of the biosynthesis of cephalosporin C. The gene may be either a cDNA or a genomic DNA. The present invention also relates to a recombinant DNA comprising a vector having inserted therein a DNA coding for at least a portion of the above-mentioned gene and being capable of expression in *Acremonium chrysogenum*, and relates to *Acremonium chrysogenum* transformed with the recombinant DNA. Furthermore, the present invention relates to a method for preparing cephalosporin C by culturing the transformed *Acremonium chrysogenum*. By this method, cephalosporin C can be prepared efficiently.

2. Discussion of Related Art

The biosynthesis of cephalosporin C proceeds according to the following sequence of reactions:

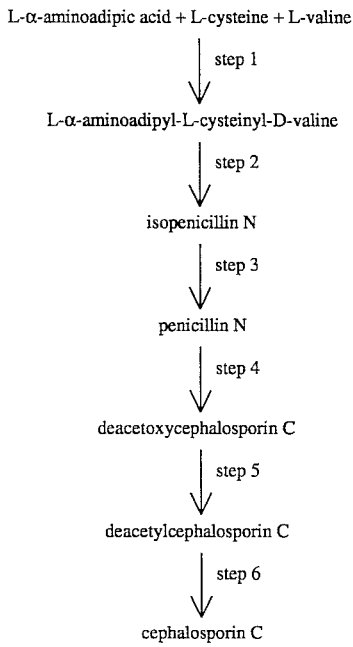

In the art, an enzyme capable of catalyzing the reaction of step 2, i.e., isopenicillin N synthetase, and enzymes capable of catalyzing the reactions of steps 3 and 4, i.e., deacetoxycephalosporin C synthetase and deacetylcephalosporin C synthetase were isolated from *Acremonium chrysogenum*. It is known that in *Acremonium chrysogenum*, a single polypeptide has both of the two enzymatic activities necessary for steps 3 and 4. Also, the genes coding for such enzymes were isolated, and the nucleotide sequences of the genes were identified. With respect to the above, reference is made to for example, Samson et al., Nature (1985) 318, 191; Dotzlaf et al., Journal of Bacteriology (1987) 169, 1611–1618; Samson et al., Biotechnology (1987) i, 1207; and Japanese Patent Application laid-Open Specification No. 63-301790.

Skatrud et al. noted that a significant amount of penicillin N, i.e., an intermediate of the above-mentioned biosynthesis of cephalosporin C, was present in the medium in which *Acremonium chrysogenum* was fermented, and introduced a vector containing a DNA fragment carrying a gene coding for deacetoxycephalosporin C synthetase/deacetylcephalosporin C synthetase (hereinafter often referred to as "DAOCS/DACS"), penicillin N being a substrate thereof, into *Acremonium chrysogenum*. As a result, Skatrud et al. succeeded in increasing the level of DAOCS/DACS in the cells and thus improving the yield of cephalosporin C [see Skatrud et al., Bio/technology (1989) 7, 477–485].

On the other hand, it was known in the art that in the above-mentioned medium in which *Acremonium chrysogenum* was fermented, a significant amount of deacetylcephalosporin C, i.e., another intermediate of the biosynthesis of cephalosporin C, was also present [see Huber et al., Applied Microbiology (1968) 16., 1011–1014]. Accordingly, an increase in the intracellular level of an enzyme capable of catalyzing the conversion of the above-mentioned intermediate to cephalosporin C (i.e., step 6 of the biosynthesis of cephalosporin C), namely, deacetylcephalosporin C acetyltransferase and a modification of the enzyme so as to be more suitable for the preparation of cephalosporin C would improve the yield of cephalosporin C.

For the above reason, the purification of deacetylcephalosporin C acetyltranserase and the isolation of a gene coding for the enzyme were strongly desired in the art.

The present inventors succeeded in isolating deacetylcephalosporin C acetyltransferase from *Acremonium chrysogenum*, and clarified that the enzyme was comprised of at least two subunits (the subunit having a molecular weight of 27,000±2000 dalton as measured by SDS polyacrylamide gel electrophoresis was designated as subunit 1 while the subunit having a molecular weight of 14,000±2000 dalton as measured by the above-mentioned electrophoresis was designated as subunit 2). Further, the present inventors determined the amino acid sequence in N-terminus portion of each of subunit 1 and subunit 2, which was as follows.

| | |
|---|---|
| (subunit 1) | Leu—X—Ala—Gln—Asp—Ile—Ala—Arg—Ile—Ser—leu—Phe—Thr—Leu—Glu—Ser—Gly—Val—Ile—Leu—Arg (wherein X indicates a site where identification of an amino acid was not made) |
| (subunit 2) | Asp—Ser—Gly—Asn—Ser—His—Arg—Ala—Gly—Gln—Pro—Ile—Glu—Ala—Val—Ser—Ser—Tyr—Leu—Arg—Tyr—Gln—Ala—Gln—Lys—Phe—Ala |

Despite various developments as mentioned above, isolation of a gene (genomic DNA) of deacetylcephalosporin C acetyltransferase has not yet been attained in the art.

SUMMARY OF THE INVENTION

With a view toward attaining a yield improvement in the biosynthesis of cephalosporin C, the present inventors have made extensive and intensive studies. As a result, the inventors have isolated a DNA comprising a cDNA coding for deacetylcephalosporin C acetyltransferase (hereinafter often referred to as "DCPCATF") from a cDNA library of *Acremonium chrysogenum*, and have determined the nucleotide sequence thereof. Further, the inventors have isolated a DNA comprising a genomic DNA of DCPC-ATF from a gene library of *Acremonium chrysogenum*, and have determined a portion of the nucleotide sequence thereof (the whole nucleotide sequence of the coding region and the nucleotide sequence of a portion of the non-coding region of the DCPC-ATF gene). As a result of still further studies, it has been found that *Acremonium chrysogenum* transformed with a recombinant DNA comprising a vector having inserted therein one of the above-mentioned DNAs (the recombinant DNA being in a form such that the DNA is capable of expression in *Acremonium chrysogenum*) exhibits improved synthetic activity of DCPC-ATF as compared to that of untransformed *Acremonium chrysogenum*. The present invention is based on these investigations and findings.

Accordingly, it is an object of the present invention to provide a novel DNA which is isolated in pure form and contains a gene coding for deacetylcephalosporin C acetyltransferase (DCPC-ATF).

It is another object of the present invention to provide a recombinant DNA capable of expression in *Acremonium chrysogenum*, which contains at least a portion of the DCPC-ATF gene.

It is a further object of the present invention to provide *Acremonium chrysogenum* transformed with the recombinant DNA, which exhibits improved synthetic activity of DCPC-ATF.

It is still a further object of the present invention to provide a method for preparing cephalosporin C by the use of the transformed *Acremonium chrysogenum*.

The foregoing and other objects, features and advantages of the present invention will be apparent from the following detailed description and appended claims taken in connection with the accompanying drawings.

BRIEF DESCRIPTION OF THE DRAWINGS

In the accompanying drawings:

FIG. 2 (*a*) and (*b*) show the nucleotide sequence (Seq. ID No. 1) of a cDNA according to the present invention coding for DCPC-ATF and the amino acid sequence (Seq. ID No. 2) coded for by the nucleotide sequence coding for a precursor of DCPC-ATF, wherein underlined portion ① indicates the biochemically determined amino acid sequence of the N-terminus region of subunit 1 mentioned hereinbefore and underlined portion ② indicates the biochemically determined amino acid sequence of the N-terminus region of subunit 2 mentioned hereinbefore;

FIG. 4(*a*) and FIG. 4(*b*) show a nucleotide sequence (Seq. ID No. 3) of 1731 bp corresponding to the portion of FIG. 3 indicated with the mark ⊢---⊣, together with the amino acid sequence (Seq. ID No. 4) of the DCPC-ATF protein which is indicated below the nucleotide sequence;

FIGS. 8–11 are graphs showing the purification degrees in the various stages of the purification operation with respect to DCPC-ATF, wherein FIG. 8 is a graph showing the results of purification of a crude enzyme solution containing DCPC-ATF by weakly basic anion exchange chromatography (1st stage), FIG. 9 is a graph showing the results of purification of the DCPC-ATF-containing eluent (obtained in the 1st stage) by hydrophobic chromatography (2nd stage), FIG. 10 is a graph showing the results of purification of the DCPC-AFT-containing eluent (obtained in the 2nd stage) by gel filtration using Sephacryl S-200 gel (3rd stage) and FIG. 11 is a graph showing the results of purification of the DCPC-ATF-containing filtrate (obtained in the 3rd stage) by high performance liquid chromatography using a weakly basic anion exchange resin (4th stage);

Figure 1:
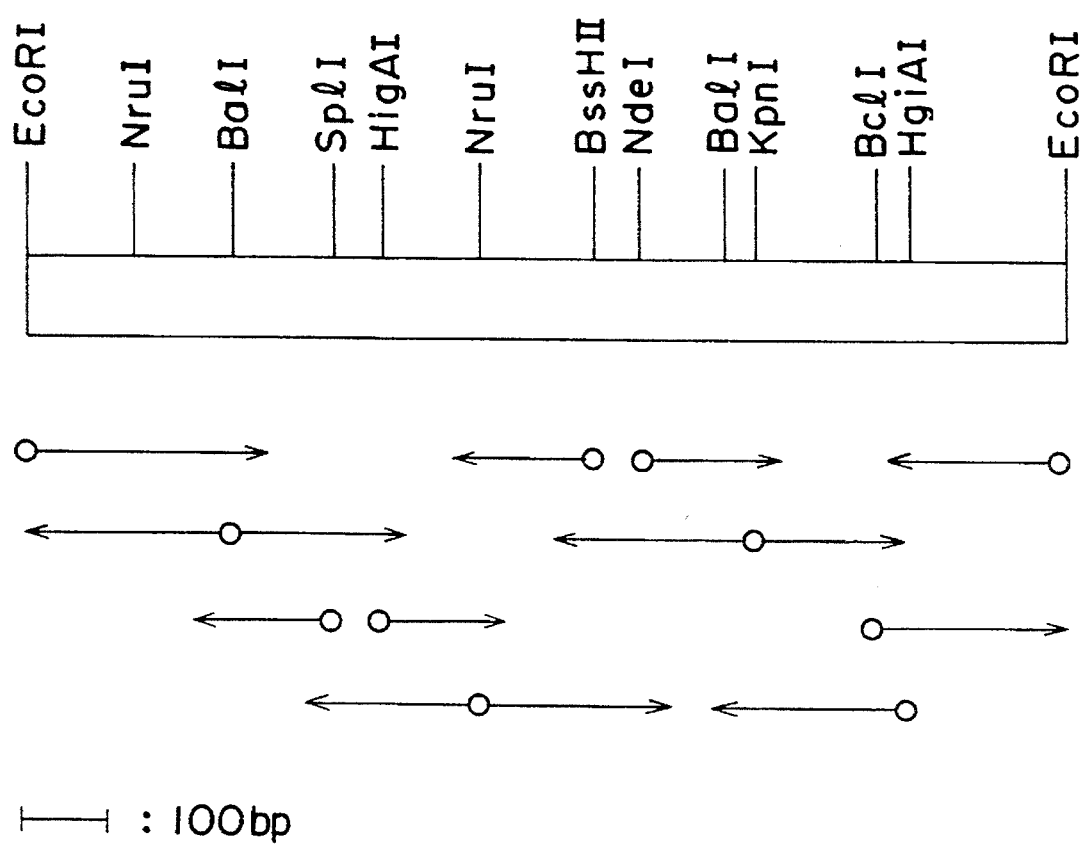
FIG. 1 shows a restriction map of DCPC-ATF cDNA insert on pCCS1 together with strategy employed for the determination of the nucleotide sequence.

In the drawings, the abbreviations have the following meanings:

| | |
|---|---|
| B: | BamHI |
| Bg: | BglII |
| B.B: | linkage site between BamHI and BglII |
| P: | PvuII |
| Ps: | PstI |
| M: | MluI |
| K: | KpnI |
| S: | SmaI |
| Sa: | SalI |
| St: | StuI |
| Sc: | ScaI |
| X: | XhoI |
| Xb: | XbaI |
| N: | NsiI |
| Nc: | NcoI |
| E: | EcoRI |
| RV: | EcoRV |
| H: | HindIII |
| Bs: | BssHII |
| Ps.Ns: | linkage site between PstI and NsiI |
| 2μ ori: | replication origin of yeast 2μ plasmid |
| CYCP: | promoter of iso-1-cytochrome C gene of yeast |
| PGKP: | promoter of *Acremonium chrysogenum* PGK gene |
| PGKT: | terminator of *Acremonium chrysogenum* PGK gene |
| ATF: | DCPC-ATF gene |
| ACTP: | promoter of *Acremonium chrysogenum* actin gene |
| ACTT: | terminator of *Acremonium chrysogenum* actin gene |
| HYB: | hygromycin B phosphotransferase gene |

Figure 6:
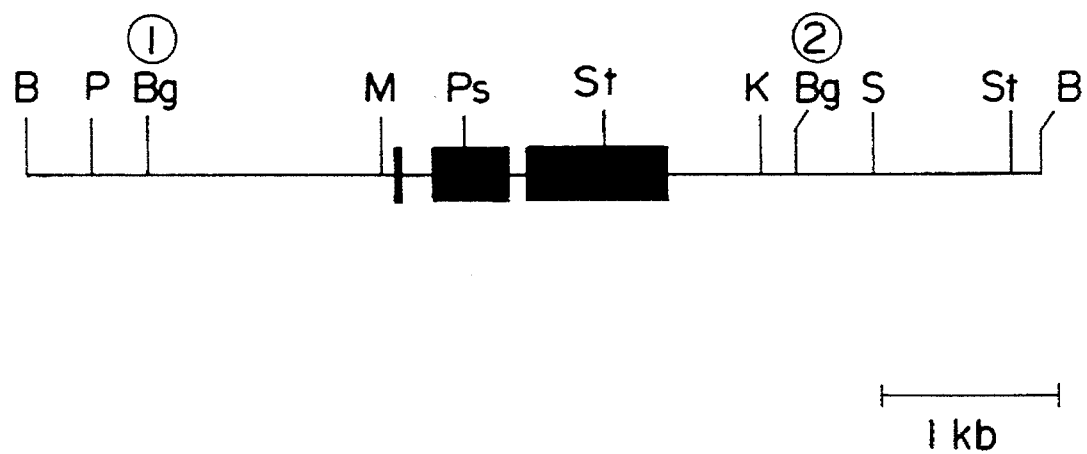
FIG. 6 shows the restriction map of a DNA fragment containing *Acremonium chrysogenum* PGK (phosphoglycerate kinase) gene.
Figure 7A:
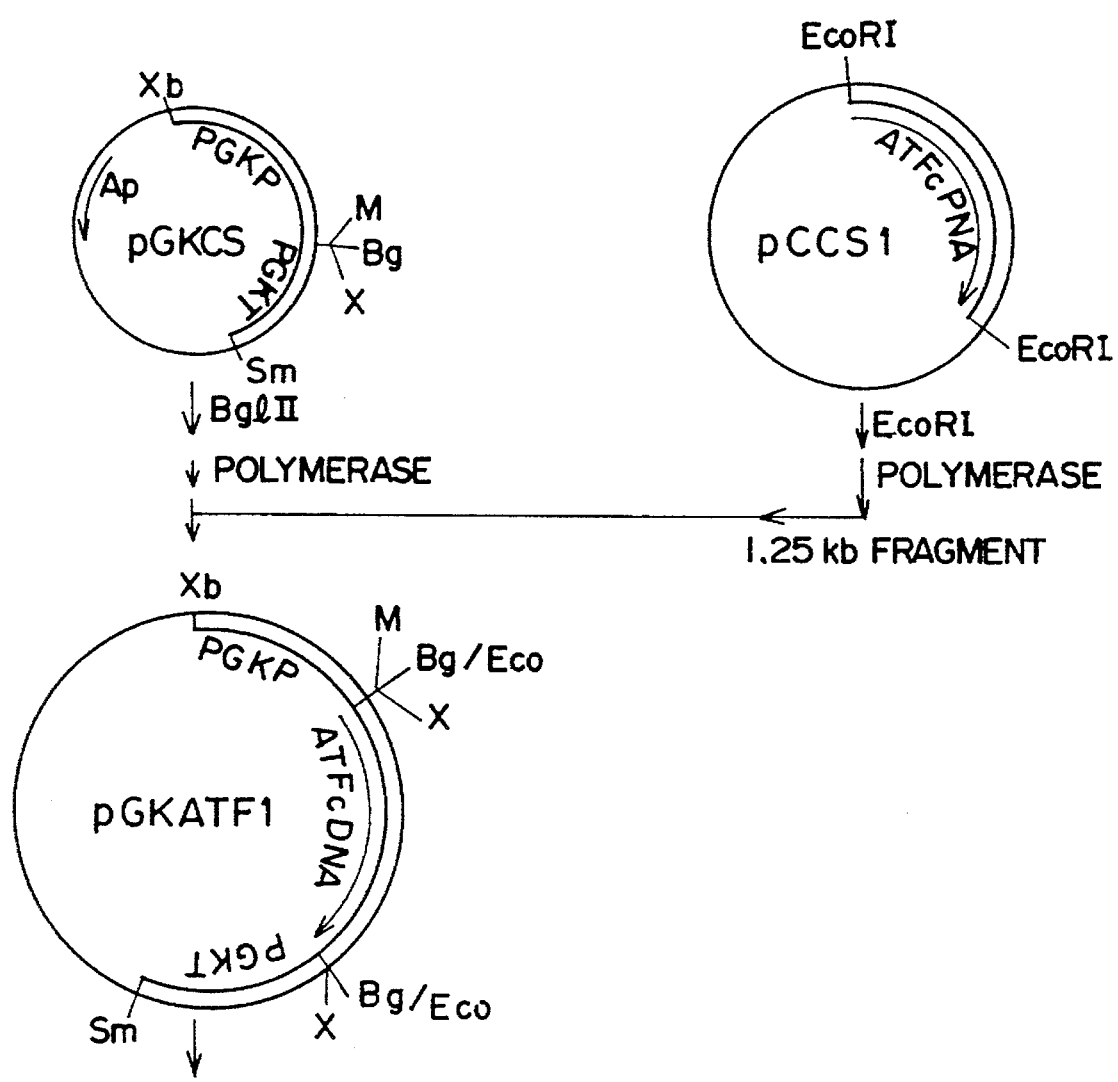
FIG. 7 (*a*) and (*b*) is a diagram showing a construction method for plasmid pTCATF1.
Figure 7:
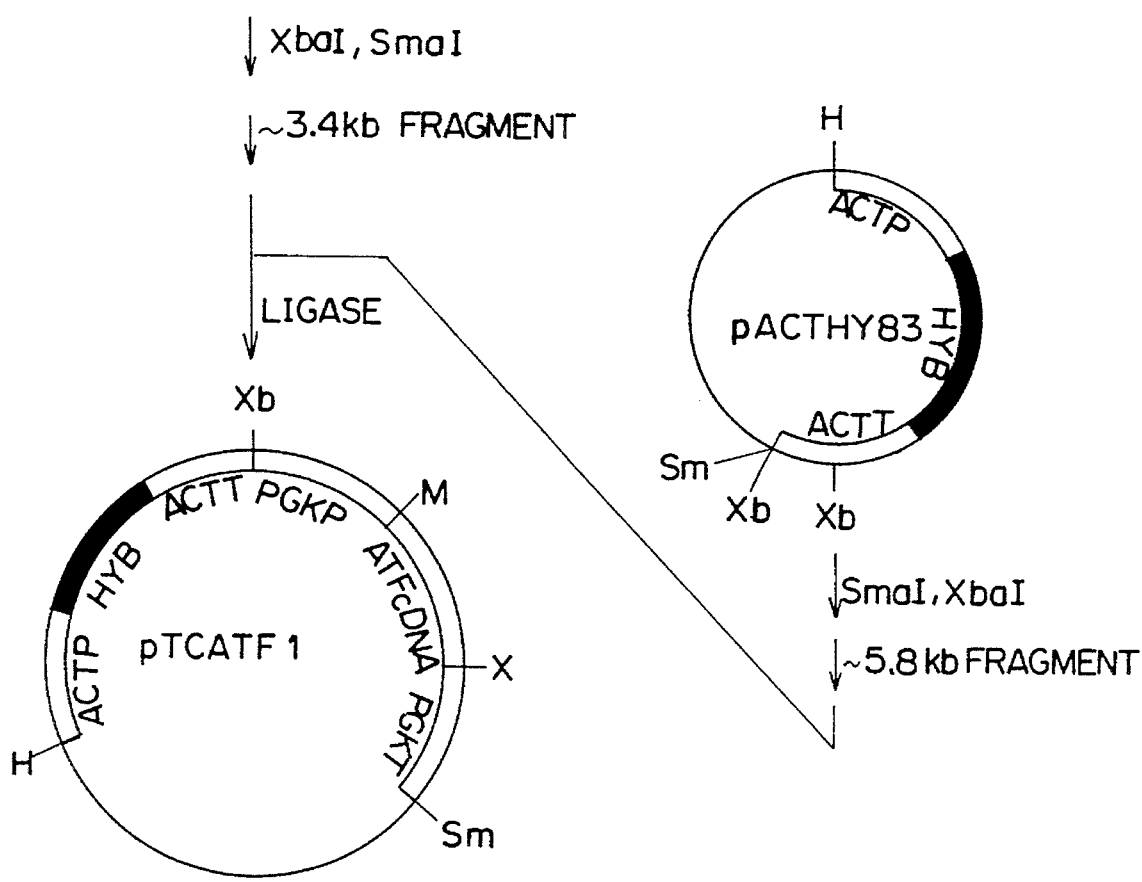
Figure 13:
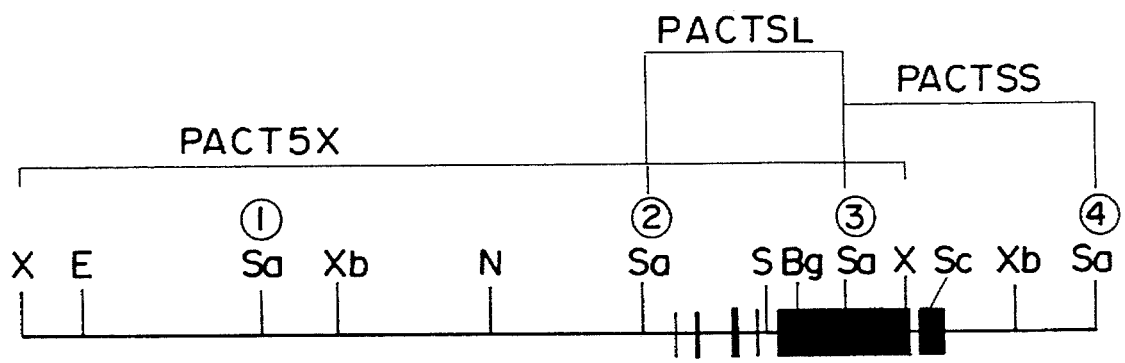
FIG. 13 shows the restriction map of a DNA fragment containing *Acremonium chrysogenum* action gene.

In FIGS. 6 and 13, mark ■ indicates exon. The 5' terminus of the first exon and the 3' terminus of the last exon have not yet been identified.

DETAILED DESCRIPTION OF THE INVENTION

Essentially, according to the present invention, an isolated DNA is provided which comprises a gene coding for DCPC-ATF. The gene can be obtained from *Acremonium chrysogenum*. The gene is either a cDNA or a genomic DNA.

It is preferred that the above-mentioned cDNA is a cDNA coding for a protein comprising an amino acid sequence represented by the following formula (I) (Seq. ID No. 4):

| Met | Ser | Pro | Gln | Ile | Ala | Asn | Arg | Phe | Glu |
|-----|-----|-----|-----|-----|-----|-----|-----|-----|-----|
| Ala | Ser | Leu | Asp | Ala | Gln | Asp | Ile | Ala | Arg |
| Ile | Ser | Leu | Phe | Thr | Leu | Glu | Ser | Gly | Val |
| Ile | Leu | Arg | Asp | Val | Pro | Val | Ala | Tyr | Lys |
| Ser | Trp | Gly | Arg | Met | Asn | Val | Ser | Arg | Asp |
| Asn | Cys | Val | Ile | Val | Cys | His | Thr | Leu | Thr |
| Ser | Ser | Ala | His | Val | Thr | Ser | Trp | Trp | Pro |
| Thr | Leu | Phe | Gly | Gln | Gly | Arg | Ala | Phe | Asp |
| Thr | Ser | Arg | Tyr | Phe | Ile | Ile | Cys | Leu | Asn |
| Tyr | Leu | Gly | Ser | Pro | Phe | Gly | Ser | Ala | Gly |
| Pro | Cys | Ser | Pro | Asp | Pro | Asp | Ala | Glu | Gly |
| Gln | Arg | Pro | Tyr | Gly | Ala | Lys | Phe | Pro | Arg |
| Thr | Thr | Ile | Arg | Asp | Asp | Val | Arg | Ile | His |
| Arg | Gln | Val | Leu | Asp | Arg | Leu | Gly | Val | Arg |
| Gln | Ile | Ala | Ala | Val | Val | Gly | Ala | Ser | Met |
| Gly | Gly | Met | His | Thr | Leu | Glu | Trp | Ala | Phe |
| Phe | Gly | Pro | Glu | Tyr | Val | Arg | Lys | Ile | Val |
| Pro | Ile | Ala | Thr | Ser | Cys | Arg | Gln | Ser | Gly |
| Trp | Cys | Ala | Ala | Trp | Phe | Glu | Thr | Gln | Arg |
| Gln | Cys | Ile | Tyr | Asp | Asp | Pro | Lys | Tyr | Leu |
| Asp | Gly | Glu | Tyr | Asp | Val | Asp | Asp | Gln | Pro |
| Val | Arg | Gly | Leu | Glu | Thr | Ala | Arg | Lys | Ile |
| Ala | Asn | Leu | Thr | Tyr | Lys | Ser | Lys | Pro | Ala |
| Met | Asp | Glu | Arg | Phe | His | Met | Ala | Pro | Gly |
| Val | Gln | Ala | Gly | Arg | Asn | Ile | Ser | Ser | Gln |
| Asp | Ala | Lys | Lys | Glu | Ile | Asn | Gly | Thr | Asp |
| Ser | Gly | Asn | Ser | His | Arg | Ala | Gly | Gln | Pro |
| Ile | Glu | Ala | Val | Ser | Ser | Tyr | Leu | Arg | Tyr |
| Gln | Ala | Gln | Lys | Phe | Ala | Ala | Ser | Phe | Asp |
| Ala | Asn | Cys | Tyr | Ile | Ala | Met | Thr | Leu | Lys |
| Phe | Asp | Thr | His | Asp | Ile | Ser | Arg | Gly | Arg |
| Ala | Gly | Ser | Ile | Pro | Glu | Ala | Leu | Ala | Met |
| Ile | Thr | Gln | Pro | Ala | Leu | Ile | Ile | Cys | Ala |
| Arg | Ser | Asp | Gly | Leu | Tyr | Ser | Phe | Asp | Glu |
| His | Val | Glu | Met | Gly | Arg | Ser | Ile | Pro | Asn |
| Ser | Arg | Leu | Cys | Val | Val | Asp | Thr | Asn | Glu |
| Gly | His | Asp | Phe | Phe | Val | Met | Glu | Ala | Asp |
| Lys | Val | Asn | Asp | Ala | Val | Arg | Gly | Phe | Leu |
| Asp | Gln | Ser | Leu | Met | ... | (I) | | | | wherein Met represents a methionine residue, Gln a glutamine residue, Asp an aspartic acid residue, Pro a proline residue, Tyr a tyrosine residue, Val a valine residue, Lys a lysine residue, Glu a glutamic acid residue, Ala an alanine residue, Asn an asparagine residue, Leu a leucine residue, Phe a phenylalanine residue, Gly a glycine residue, His a histidine residue, Ser a serine residue, Thr a threonine residue, Ile an isoleucine residue, Trp a tryptophan residue, Arg an arginine residue, and Cys a cysteine residue, and the left and right ends of formula (I) represent the N-terminus and C-terminus, respectively, or coding for a variant of the above-mentioned protein which has an activity to acetylate deacetylcephalosporin C into cephalosporin C.

More preferably, the above-mentioned cDNA comprises a nucleotide sequence represented by the following formula (II) (Seq. ID No. 5):

```
ATGTCGCCTCAGATCGCCAA
TCGCTTCGAGGCTTCGCTAG
ATGCCCAAGACATAGCCAGA
```

-continued

```
ATATCGCTCTTCACACTGGA
ATCTGGCGTCATCCTTCGCG
ATGTACCCGTGGCATACAAA
TCGTGGGGTCGCATGAATGT
CTCAAGGGATAACTGCGTCA
TCGTCTGCCACACCTTGACG
AGCAGCGCCCATGTCACCTC
GTGGTGGCCCACACTGTTTG
GCCAAGGCAGGGCTTTCGAT
ACCTCTCGCTACTTCATCAT
CTGCCTAAATTATCTCGGGA
GCCCCTTTGGGAGTGCTGGA
CCATGTTCACCGGACCCCGA
TGCAGAAGGCCAGCGCCCGT
ACGGGGCCAAGTTTCCTCGC
ACGACGATTCGAGATGATGT
TCGTATTCATCGCCAGGTGC
TCGACAGGTTAGGCGTCAGG
CAAATTGCTGCCGTAGTCGG
CGCATCCATGGGTGGAATGC
ACACTCTGGAATGGGCCTTC
TTTGGTCCCGAGTACGTGCG
AAAGATTGTGCCCATCGCGA
CATCATGCCGTCAGAGCGGC
TGGTGCGCAGCTTGGTTCGA
GACACAGAGGCAGTGCATCT
ATGATGACCCCAAGTACCTG
GACGGGGAGTACGACGTAGA
CGACCAGCCTGTCCGGGGGC
TCGAAACAGCGCGCAAGATT
GCGAATCTCACGTACAAGAG
CAAACCTGCGATGGACGAGC
GCTTCCATATGGCTCCAGGA
GTCCAAGCCGGCCGGAATAT
CAGCAGCCAGGATGCGAAGA
AGGAAATCAACGGCACAGAC
AGCGGCAACAGCCACCGTGC
TGGCCAGCCCATTGAAGCCG
TATCTTCCTATCTCCGGTAC
CAGGCCCAGAAGTTTGCCGC
GAGCTTCGACGCCAACTGCT
ACATCGCCATGACACTCAAG
TTCGACACCCACGACATCAG
CAGAGGCCGGGCAGGATCAA
TCCCGGAGGCTCTGGCAATG
ATTACACAACCAGCGTTGAT
CATTTGCGCCAGGTCAGACG
GTCTGTACTCGTTTGACGAG
CACGTTGAGATGGGGCGCAG
TATCCCAAACAGTCGTCTTT
GCGTGGTGGACACGAATGAG
GGTCATGACTTCTTTGTAAT
GGAAGCGGACAAGGTTAATG
ATGCCGTCAGAGGATTCCTC
GATCAGTCATTAATGTGA
...(II)
``` wherein A represents a deoxyadenylic acid residue, G a deoxyguanylic acid residue, C a deoxycytidylic acid residue and T a thymidylic acid residue, and the left and right ends of formula (II) represent the 5'-terminus and 3'-terminus, respectively, or comprises a nucleotide sequence which is obtained by substituting at least one nucleotide of the nucleotide sequence of formula (II) in accordance with the degeneracy of the Genetic Code.

The DNA of the present invention which comprises a cDNA coding for DCPC-ATF can be produced according to the below outlined steps of:

(1) extracting a total RNA from *Acremonium chrysogenum* having an activity to produce cephalosporin C, followed by separation and concentration of a m-RNA fraction;

(2) synthesizing a single-stranded cDNA and then a double-stranded cDNA by using the above-mentioned mRNA as a template, followed by incorporation of the same into a suitable phage vector to thereby obtain a cDNA library of *Acremonium chrysogenum*;

(3) chemically synthesizing a mixture of oligonucleotides comprising all genetically feasible DNA nucleotide sequences which could be presumed from a portion of the amino acid sequence of DCPC-ATF determined by the present inventors or chemically synthesizing an oligonucleotide comprising a nucleotide sequence presumed by considering the frequency of codon usage, such oligonucleotides being designated as "DNA probe";

(4) labeling the DNA probe with $^{32}$p, performing a plaque hybridization with the cDNA library obtained in step (2) above, and selecting and separating phages having been positive; and (5) extracting a DNA from the separated phages, determining the nucleotide sequence of the cDNA incorporated in the vector, and comparing the amino acid sequence of a protein obtained by translation of the nucleotide sequence of the resultant cDNA with the biochemically determined partial amino acid sequence of the subunits of DCPC-ATF to confirm whether the obtained cDNA codes for DCPC-ATF.

General procedure regarding the use and handling of RNA and DNA in the above steps is conventional, which is described in for example, T. Maniatis et al., Molecular Cloning A Laboratory Manual, Cold Spring Harbor Laboratory, 1982. With respect to all of the enzymes, agents and vectors for use in cDNA cloning which are used in the above steps, commercial products may be utilized. The enzymes, agents and vectors may be successfully utilized in accordance with the protocols attached to the products, unless otherwise specified.

In step (1) above, *Acremonium chrysogenum* ATCC 11550, preferably *Acremonium chrysogenum* ATCC 36225 and *Acremonium chrysogenum* IS-5, may be used as an RNA extraction source. The above-mentioned *Acremonium chrysogenum* IS-5 was placed on deposit in the Fermentation Research Institute, Agency of Industrial Science and Technology, Ministry of International Trade and Industry, Japan on Jan. 29, 1990, and was given Accession No. P-11232, which was then transferred to the Budapest Treaty deposit on Nov. 5, 1990 under Accession No. FERM BP-3153. Extraction of total RNA from *Acremonium chrysogenum* may be carried out in accordance with the method as described in for example, Boel et al., EMBO Journal (1984) 3, 1097–1102. The synthesis of cDNA in step (2) above may be carried out in accordance with the conventional method as described in for example, Gubler-Hoffman et al., Gene (1983) 25, 263. The synthesis of a mixture of oligonucleotides comprising a nucleotide sequence defined in step (3) above may be carried out using a commercial DNA synthesizer in accordance with the protocol attached thereto. The determination of the DNA nucleotide sequence in step (5) above may be carried out in accordance with the conventional dideoxy method [see Sanger et al., Proc. Nati. Acad. Sci. USA (1977) 73, 5463].

The DNA of the present invention comprising a genomic DNA can be produced by the below-outlined steps:

(i) extracting a total DNA from *Acremonium chrysogenum*, and performing partial cleavage of the DNA with a suitable restriction enzyme, such as MboI and the like;

(ii) incorporating the DNA fragments obtained in step (i) above in a suitable phage vector (such as EMBL 3, EMBL 4, and the like) to thereby produce genomic DNA library of *Acremonium chrysogenum*;

(iii) selecting and isolating the desired phage from the library obtained in step (ii) above by plaque hybridization using a DNA probe;

(iv) extracting a total DNA from the selected phage, performing Southern hybridization using the above-mentioned probe, so that the desired gene is identified on a restriction enzyme-cleaved fragment of appropriate size, which is subcloned to a conventional plasmid vector; and (v) determining the nucleotide sequence of the thus obtained DNA fragment, confirming the presence of DCPC-ATF genomic DNA by a comparison with the nucleotide sequence coding for the known amino acid sequence or the above-obtained cDNA to thereby determine the coding region thereof.

With respect to manipulations regarding the above materials and process, general procedures for *E. coli*, phage and DNA are well known in the art, and can be performed easily, for example, by the use of reference books, such as one written by Maniatis et al., (see T. Maniatis et al., "Molecular Cloning A Laboratory Manual", Cold Spring Harbor Laboratory 1982, 1989). Commercial products are available for enzymes, reagents and vector DNA, and unless otherwise specified, the purpose can be perfectly met when they are used under their specifications. In step (i) above, for example, a strain, such as *Acremonium chrysogenum* ATCC 11550 and *Acremonium chrysogenum* IS-5, is used as a DNA extraction source.

The extraction of a total DNA from *Acremonium chrysogenum* can be conducted by a method, such as one by Johnstone et al. [see Johnstone et al., EMBO Journal (1985) 4, 1307–1311] and one by Minuth et al. [see Minuth et al., Current Genetics (1982) 5, 227–231].

In step (iii) above, the probe useful for selecting a clone containing the DCPC-ATF gene includes a cDNA fragment coding for DCPC-ATF, for example, a cDNA insert of pCCS1 as described in Example 1. An appropriate DNA oligomer may be synthesized on the basis of the nucleotide sequence of the above-mentioned cDNA to be used as a probe. The synthesis of the DNA oligomer can be performed by the use of a commercially available DNA synthesizer with the aid of the detailed manipulation protocol attached thereto. The nucleotide sequence of the DNA in step (v) above can be determined by the conventional dideoxy method [see Sanger et al., Proc. Nati. Acad. Sci. USA (1977) 73, 5463].

In another aspect of the present invention, there is provided a recombinant DNA capable of replication in a host cell is provided, which comprises a vector having inserted therein at least a portion of the above-mentioned DNA comprising a cDNA or a genomic DNA, the portion coding for a protein having an activity to acetylate deacetylcephalosporin C into cephalosporin C, the recombinant DNA being in a form such that the portion is capable of expression in *Acremonium chrysogenum*. The terminology "in a form such that the portion is capable of expression in *Acremonium chrysogenum*" used above means that in the case of the cDNA, a vector containing a promoter, a terminator and the like derived from *Acremonium chrysogenum* is used so as for the resultant recombinant DNA to be capable of expression, and that in the case of the genomic DNA comprised only of the coding region, incorporation of a promoter, a terminator and the like as mentioned above with respect to cDNA is necessary so as for the resultant recombinant DNA to be capable of expression, whereas in the case of the genomic DNA already containing such a promoter and a terminator, the recombinant DNA containing the genomic DNA as such is capable of expression.

As the above-mentioned promoter and terminator derivable from *Acremonium chrysogenum*, there may be mentioned promoters and terminators derived from *Acremonium chrysogenum* PGK gene (described in Reference Example 2 below), *Acremonium chrysogenum* actin gene (described in Reference Example 3) and *Acremonium chrysogenum* isopenicillin N synthetase gene [see for example, Paul L. Skatrud et al. curr. Genet. (1987) 12, 337–348].

Examples of vectors for use in the transformation of *Acremonium chrysogenum* include pACTHY83 (see Reference Example 2). With respect to the vectors for use in the transformation of *Acremonium chrysogenum*, reference is made to for example, Skatrud et al., Bio/technology (1989) 7, 477–485. The transformation of *Acremonium chrysogenum* can be carried out by a method, such as one by Queener et al. [see Queener et al., Microbiology 1985, American Society for Microbiology (1985) pp 468–472] or by Isogai et al. [see Isogai et al., Agric. Biol. Chem. (1987) 51, 2321–2329].

In a further aspect of the present invention, there is provided *Acremonium chrysogenum* transformed with the above-mentioned recombinant DNA.

The DCPC-ATF activity of the obtained transformant is increased, so that the effect of the introduction of the DNA of the present invention can be achieved.

In still a further aspect of the present invention, there is provided a method for preparing cephalosporin C which comprises culturing the above-mentioned *Acremonium chrysogenum* transformed with the recombinant DNA to produce cephalosporin C, and isolating the cephalosporin C.

The culturing is performed in a culture medium for use in the biosynthesis of cephalosporin C at a temperature of from 25° to 30° C., the culture medium having a pH value of from 6 to 7. With respect to the culture medium, reference is made to for example, Queener S.W. et al., In: Biotechnology of Industrial Antibiotics. E.J. Vandamme, Marcel Dekker Inc., N.Y., Basel, pp141–170.

When the DNA of the present invention is ligated to a vector in a form such that the DNA is capable of expression in *Acremonium chrysogenum* and introduced into *Acremonium chrysogenum*, the level of DCPC-ATF in the cells can be raised so that the ability to produce cephalosporin C can be improved. Further, by using the DNA of the present invention as a probe, the analysis of the DCPC-ATF gene with respect to its expression and control mechanisms or the like can be conducted on a molecular level. Moreover, the DNA of the present invention can be advantageously used for the mass production of DCPC-ATF and its precursor.

Furthermore, it is noted that by utilizing the DNA comprising a genomic DNA according to the present invention, the DCPC-ATF gene present in *Acremonium chrysogenum* can be destroyed in a conventional manner [see for example, Bruce L. Miller, et al: Molecular and Cellular Biology (1985), 1714–1721; and David W. Holden et al.: The EMBO Journal (1989), 1927–1934] so that a novel *Acremonium chrysogenum* can be created, which can efficiently produce deacetylcepharosporin C. Deacetylcephalosporin C is an important starting material for preparing cephalosporin antibiotics, as is cephalosporin C.

DETAILED DESCRIPTION OF THE PREFERRED EMBODIMENTS

The present invention will hereinafter be described with reference to the following Examples, which should not be construed to be limiting the present invention.

Abbreviations employed hereinafter are as follows.

CM culture medium: medium comprised of 20 g of sucrose, 0.5 g of potassium dihydrogen phosphate, 0.5 g of dipotassium hydrogen phosphate, 0.5 g of potassium chloride, 0.5 g of magnesium sulfate.$7H_2O$, 0.01 g of ferrous (II) sulfate.$7H_2O$, 3 g of sodium nitrate, 4 g of yeast extract, and 10 g of peptone in 1 liter of distilled water.

CM solid medium: medium of CM culture medium containing 1.5% of agar.

GA culture medium: medium comprised of 40 g of glucose, 4 g of asparagine, 0.1 g of calcium chloride, 0.1 g of sodium chloride, 25 ml of trace metal solution comprised of 4 g of magnesium sulfate.$7H_2O$, 0.4 g of ferrous (II) sulfate.$7H_2O$, 0.16 g of manganese sulfate.$4H_2O$, 0.4 g of zinc sulfate-$7H_2O$, and 0.04 g of anhydrous copper sulfate dissolved in 1 liter of distilled water, and 30 ml of 0.1M phosphate buffer solution (pH 7.0) in 1 liter of distilled water.

GAG culture medium: same as GA culture medium except that glycerol is used as glucose 6×SSC: 0.9 M sodium chloride/90 mM sodium citrate 20×SSPE: solution of 210 g of sodium chloride, 31.2 g of sodium dihydrogen phosphate.$2H_2O$ and 40 ml of 0.5 M EDTA (Ethylenediamine tetraacetic acid) in 1 liter of distilled water.

50×Denhardt's: solution of 5 g of Ficoll, 5 g of polyvinyl pyrrolidone and 5 g of bovine serum albumin in 500 ml of distilled water.

20×SET: 3 M sodium chloride/0.4 M tris buffer (pH 7.8)/20 mM EDTA.

N-3 seed culture medium: medium comprised of 40 g of corn steep liquor, 20 g of beet, 2 g of ammonium acetate, and 40 g of a hydrochloric acid hydrolysate of starch dissolved in 1 liter of distilled water.

Main culture medium: medium comprised of 30 g of beet, 40 g of defatted soy bean, 10 g of corn steep liquor, 5 g of ammonium acetate, 7 g of ammonium sulfate, 8 g of calcium sulfate, 15 g of calcium carbonate, 60 g of a hydrochloric acid hydrolysate of starch and 41.5 g of methyl oleate dissolved in 1 liter of distilled water.

P-buffer: 0.6 M potassium chloride, 0.01 M magnesium chloride, and 0.025 M calcium chloride.

PEG solution: 25% polyethylene glycol (about 4000), 0.01M tris buffer (pH8.0), 0.05 M calcium chloride, and 0.6 M potassium chloride.

ATF stabilizing buffer: 15% ethylene glycol, 10 mM dithiothreitol, 10 mM 7-aminocephalosporanic acid, 1 mM EDTA, and 1 mM para-amidinophenylmethane-sulfonyl fluoride hydrochloride.

EXAMPLE 1

I. Production of DNA containing DCPC-ATF cDNA

Step (1) Incubation of *Acremonium chrysogenum*

Mycellia of *Acremonium chrysogenum* IS-5 cultivated at 30° C. for 5 days on CM solid medium are inoculated in 50 ml of CM culture medium, followed by incubation at 30° C. for 3 days. The resultant culture medium is inoculated in 500 ml of GA culture medium, followed by incubation at 30° C. for 20 hr.

Step (2) Extraction of m-RNA

Mycellia suspension obtained in step 1 is filtered under reduced pressure, and collected mycellia (about 10 g in the wet state) is frozen in liquid nitrogen. The resultant frozen mycellia is reduced to powder using a mortar and a pestle. The thus obtained powder is suspended in 30 ml of a solution containing 100 mM sodium acetate, 2.5 mM EDTA and 4% SDS (sodium dodecylsulfate), and then subjected to extraction by an equal volume of a solution containing phenol, chloroform, and isoamylalcohol (50:50:1), and to centrifugation at 10,000 rpm for 20 min, to thereby collect the water layer. The resultant liquid phase is furthermore centrifuged at 30,000 rpm for 40 min to remove any insoluble matter. 10 g of cesium chloride is dissolved in 25 ml of the resultant supernatant to obtain a solution, and the solution is superposed on 7 ml of a solution containing 5.7 M cesium chloride and 0.1 M EDTA dispensed in an ultracentrifuge tube. The tube is subjected to 20,000 rpm centrifugation at 25 ° C. for 17 hr to thereby collect total RNA as a precipitate. The precipitate of RNAs is washed with 95% ethanol, dried, and then dissolved in 1 ml of distilled water. Proteinous foreign matter is removed by extraction using a solution of chloroform and butanol (4:1). RNAs are recovered from the solution by precipitation with ethanol. The resultant RNAs are dissolved in a 10 mM tris-HC1 buffer solution (pH 7.5) containing 1 mM EDTA, 0.1% SDS, and 0.5 M lithium chloride, incubated at 68 ° C. for 3 min, rapidly cooled and subjected to chromatography using an oligo dT cellulose column. Adsorbed m-RNA having poly A is eluted by a 10 mM tris HC1 buffer solution containing 1 mM EDTA and 0.1% SDS, and m-RNA is recovered by precipitation with ethanol. By the above procedure, 80 µg of m-RNA is obtained.

Step (3) Preparation of cDNA library

Using cDNA synthesizing system (manufactured and sold by Amersham International, England), a double stranded cDNA is synthesized from the m-RNA (4 µg) obtained in step 2 via a single strand cDNA formation according to the protocol attached to the system. Methylation at the EcoRI restriction site present inside the resultant double stranded cDNA, addition of an EcoRI linker to the terminus of DNA, cleaving with an EcoRI and the removal of free linker by gel filtration are carried out by the use of cDNA-cloning system-λgt-10 (manufactured and sold by Amersham International, England) according to the procedure written in the protocol, thereby obtaining about 200 ng of double stranded cDNA having EcoRI restriction site at the terminus thereof. On the other hand, λ-gt-10DNA (manufactured and sold by Stratagene Co., Ltd., USA) is subjected to the following treatments, i.e., digestion with EcoRI and subsequent removal of 5'-phosphate group by alkaline phosphatase. Then, the resultant dephosphated λ-gt-10DNA fragment (1 µg) is ligated with 100 ng of the double stranded cDNA by the use of T4 ligase. The resultant ligated fragment is inserted into λ-phage particles using Gigapack Gold (Packaging Extract sold by Stratagene Co., Ltd., USA). Recombinant phage suspension obtained above is diluted in an appropriate concentration, and *E. coli* NM514 is infected with the diluted recombinant phage suspension. The number of plaques which have appeared is counted. As a result, it is observed that the suspension contains about $2 \times 10^5$ recombinant phages. This phage suspension is designated as cDNA library of *Acremonium chrysogenum* and stored at 4° C.

Step (4) Preparation of DNA probe

The present inventors have previously purified DCPC-ATF from *Acremonium chrysogenum*, and have demonstrated that the enzyme has two kinds of subunits with different molecular weights (hereinafter, the subunit with larger molecular weight is designated as subunit 1 and the subunit with smaller molecular weight as subunit 2). The amino acid sequence in N-terminus of each of both the subunits have been determined as shown in formula 1 (the sequence of subunit 1 Seq. ID No. 6) and formula 2 (sequence of subunit 2 Seq. ID No. 7).

| | |
|---|---|
| Formula 1: | Leu—X—Ala—Gln—Asp—Ile—Ala—Arg—Ile—Ser—Leu—Phe—Thr—Leu—Glu—Ser—Gly—Val—Ile—leu—Arg |
| Formula 2: | Asp—Ser—Gly—Asn—Ser—His—Arg—Ala—Gly—Gln—Pro—Ile—Glu—Ala—Val—Ser—Ser—Tyr—Leu—Arg—Tyr—Gln—Ala—Gln—Lys—Phe—Ala |

An oligonucleotide mixture comprising all genetically feasible DNA nucleotide sequences presumed from the amino acid sequence underlined in formula 1 is synthesized, and designated as LN1. LN1 is a mixture of 48 kinds of 14-mer oligonucleotides corresponding to the DNA chain complementary with m-RNA, and has the following sequence Seq. ID No. 8.

5'GC(GAT)AT(GA)TC(TC)TG(GATC)GC3'

The parenthesis indicates a location where a mixture of nucleotides is used.

Then, an oligonucleotide which has a nucleotide sequence presumed from the amino acid sequence underlined in formula 2 is synthesized and designated as SN1. SN1 is a specific 59 mer oligonucleotide presumed and designed by considering the frequency of codon usage of *Acremonium chrysogenum*, and possesses the following sequence Seq. ID No. 9.

5'GCCGGCCAGCCCATCGAGGCCGTCTCCTCCTACCTCCG
CTACCAGGCCCAGAAGTTCGC3'

The synthesis of LN1 and SN1 mentioned above is performed using DNA synthesizer model 380-A (manufactured and sold by Applied Biosystems, USA). The resultant LN1 and SN1 are labeled with $^{32}$p, by the use of T4 polynucleotide kinase and γ-$^{32}$P-ATP according to the method descried in the Laboratory Manual by Maniatis, and the labeled LN1 and SN1 are used in the hybridization reaction mentioned below. Hereinafter, the labeled probes obtained above are designated as $^{32}$P-LN1 and $^{32}$P-SN1.

Step (5) Screening by hybridization

E.coli NM514 is infected with a portion of the phage suspension obtained in Step (3) to thereby form a total of $1.6 \times 10^4$ plaques on four plates. These plaques are transferred to a nitrocellulose filter according to the method by Benton et al. [see Benton et al., Science (1977) 196, 180–182]. Transferred DNA is denatured with alkali, neutralized, and then fixed.

The fixed DNA is hybridized with the probe $^{32}$P-SN1 obtained in step 4. Hybridization is performed with a solution containing 30% formamide, 5×Denhardt's, 5×SSPE, 0.1% SDS and $5 \times 10^5$ cpm/ml $^{32}$P-SN1 at 42° C. for 14 hr. Then, the filter is washed twice with 1×SSC containing 0.1% SDS at room temperature for 15 min, and further washed with 0.2×SSC containing 0.1% SDS at 50° C. for 20 min.

Subsequently, using an intensifier screen, autoradiography is conducted at −80° C. for 22 hr. As a result, ten positive spots are found. A phage is extracted from the agar medium corresponding to four positive spots, and again subjected to plaque hybridization according to the method mentioned above to thereby obtain four types of purified phage clones. From the four phage clones obtained above, recombinant cDNA is extracted using the method of Grossberger et al. [see Grossberger et al., Nucleic Acids, Research (1987) 15, 6737]. The resultant λDNAs are designated as λCCS1, λCCS2, λCCS3, and λCCS4, respectively.

Then, these λDNAs are digested with EcoRI, followed by agarose gel electrophoresis, and subsequently, southern hybridization is performed using the above-mentioned probes, $^{32}$P-SN1 and $^{32}$P-LN1 [with regard to the method, see Southern et al., Journal of Molecular Biology (1975) 98, 503–517]. The result shows that the cDNA inserts, i.e., cDNA fragments cleaved with EcoRI, in the clones (from λCCS1 to λCCS4), hybridize strongly with not only probe SN1 but also probe LN1. This fact strongly suggests that the cDNA codes for two subunits forming DCPC-ATF, and in other words that the information coding for both subunit 1 and subunit 2 is present on the same m-RNA.

Hybridization using $^{32}$P-SN1 and washing of the filter are performed in substantially the same manner as the plaque hybridization mentioned above. When $^{32}$P-LN1 is used, hybridization is conducted at 35° C. for 6 hr by the use of a solution containing 6×SET, 5×Denhardt's, 0.1% SDS and $10^5$–$10^6$ cpm/ml $^{32}$P-LN1. The resultant filter is washed with 6×SSC at room temperature for 3 min, and then at 40° C. for 3 min with the same solution, followed by measurement with autoradiography.

Step (6) Subcloning of cDNA fragments and the mapping of partial restriction fragments After digesting the above-mentioned λCCS1 with EcoRI, the digested λCCS1 is subjected to agarose gel electrophoresis to prepare a cDNA fragment of 1.25 kb hybridized with SN1 and LN1, which is subjected to subcloning into the EcoRI site of pUC 19. One of the thus obtained plasmids is designated as pCCS1, which is digested with the various restriction enzymes and then subjected to agarose electrophoresis. As a result, a restriction map of cDNA insert of 1.25 kb shown in FIG. 1 is obtained.

In the procedure discussed above, the preparation of DNA fragment from agarose gel is performed with Gene Clean (Gene Clean, sold by Funakoshi Pharmaceutical Co., Ltd., Japan) according to the protocol attached thereto. Basic operations, such as subcloning a DNA fragment into a plasmid, ligation of a plasmid with a DNA fragment, transformation of E.coli, and preparation and analysis of the plasmid obtained by subcloning, are conducted in substantially the same manner as the method described in the Laboratory Manual by Maniatis.

Step (7) Determination of cDNA nucleotide sequence

The total DNA nucleotide sequence of the cDNA fragment of 1.25 kb described above is determined by the method of Sanger et al. Practically, the determination of the nucleotide sequence is conducted using Takara's sequencing kit (manufactured and sold by Takara Shuzo Co., Ltd., Japan). The strategy of determining nucleotide sequence is shown in the bottom part of the restriction map of FIG. 1. In the map, the arrow indicates the direction and extent of sequence determination. The thus determined DNA nucleotide sequence is demonstrated in FIGS. 2(a) and 2(b).

There is an open reading frame from an initiation codon (ATG) starting at 35th nucleotide through a termination codon (TGA) ending at 1192nd nucleotide, which codes for a polypeptide of 385 amino acids. The amino acid sequence translated from the open reading frame is shown under the nucleotide sequence in FIG. 2. In the above-mentioned amino acid sequence, the amino acid sequence from 13th Leu to 32nd Leu is completely in agreement with the N-terminus amino acid sequence of subunit 1 forming DCPC-ATF which is determined by biochemical techniques except for the second unidentified amino acid. Furthermore, in the amino acid sequence, the amino acid sequence from 260th Asp to 286th Ala perfectly coincides with that of the N-terminus in subunit 2. The molecular weights of both protein of from 13th leu to 259th Thr and protein of from of 260th Asp to 385th Met are calculated to be 27600 and 13894, respectively, and these molecular weights are in good agreement with those of subunit 1 and subunit 2 biochemically determined by the use of SDS polyacrylamidogel electrophoresis.

From the results obtained above, it is apparent that the thus derived cDNA in the present invention codes for the DCPC-ATF precursor.

II. Construction of pTCATF1 for Expression in *Acremonium chrysogenum*

Figure 8:
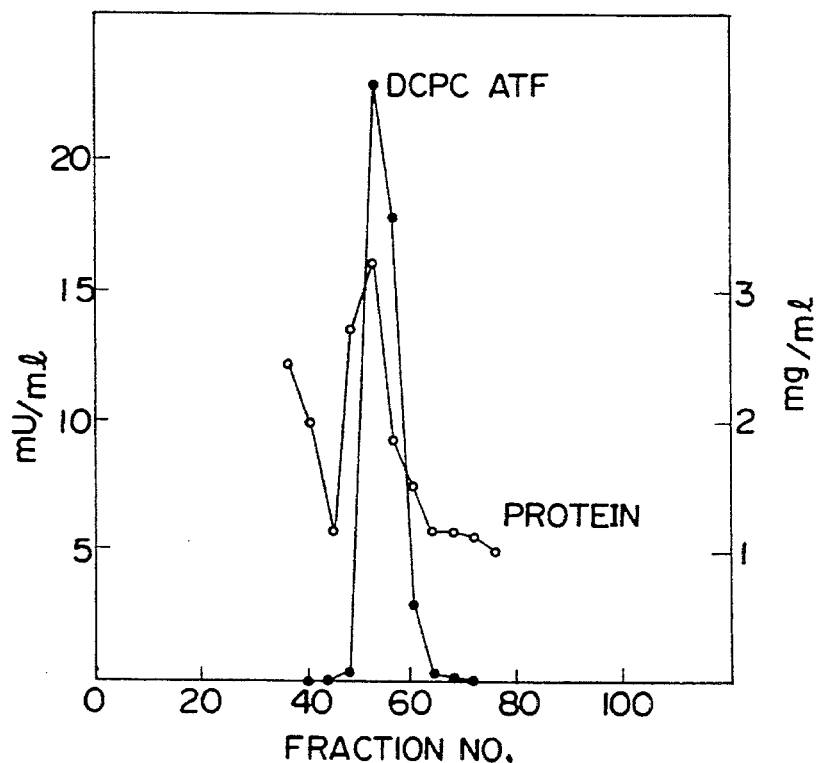
Figure 9:
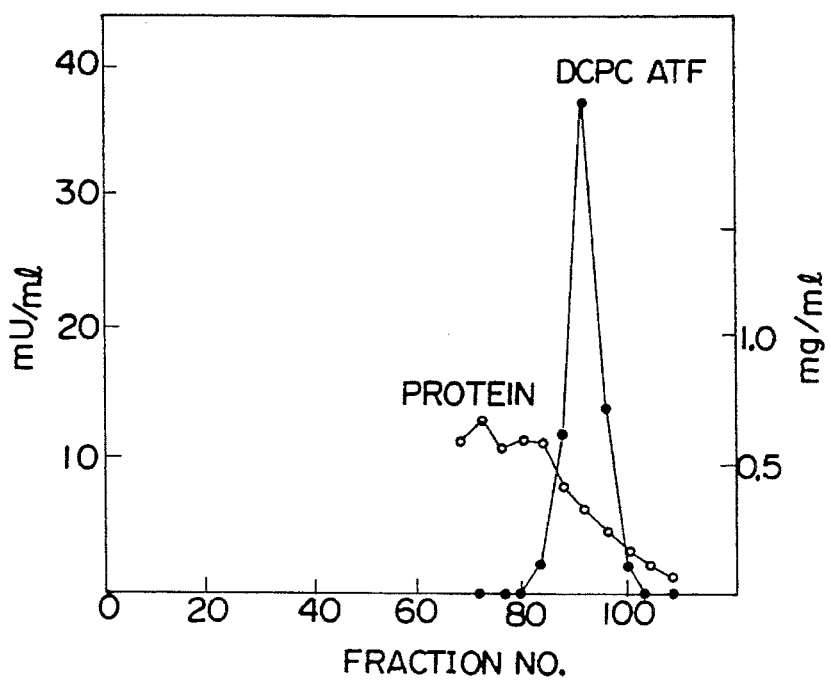
Figure 10:
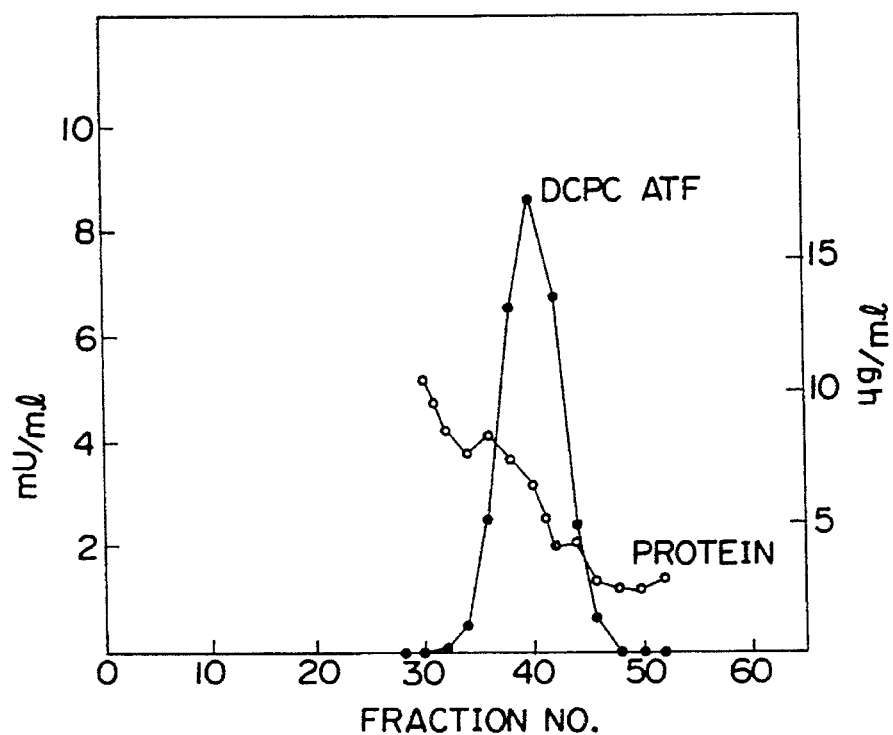
Figure 11:
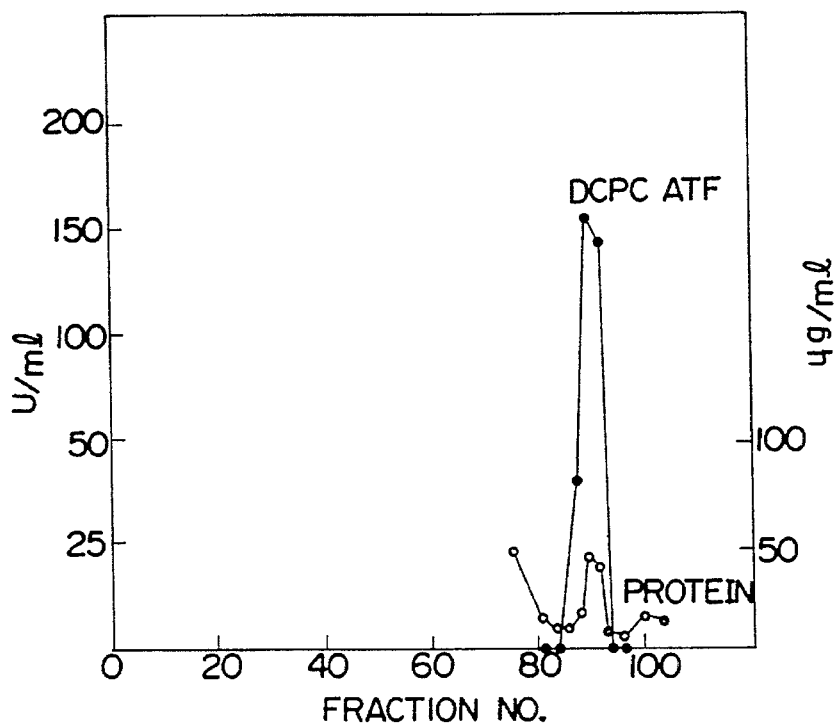
Figure 12:
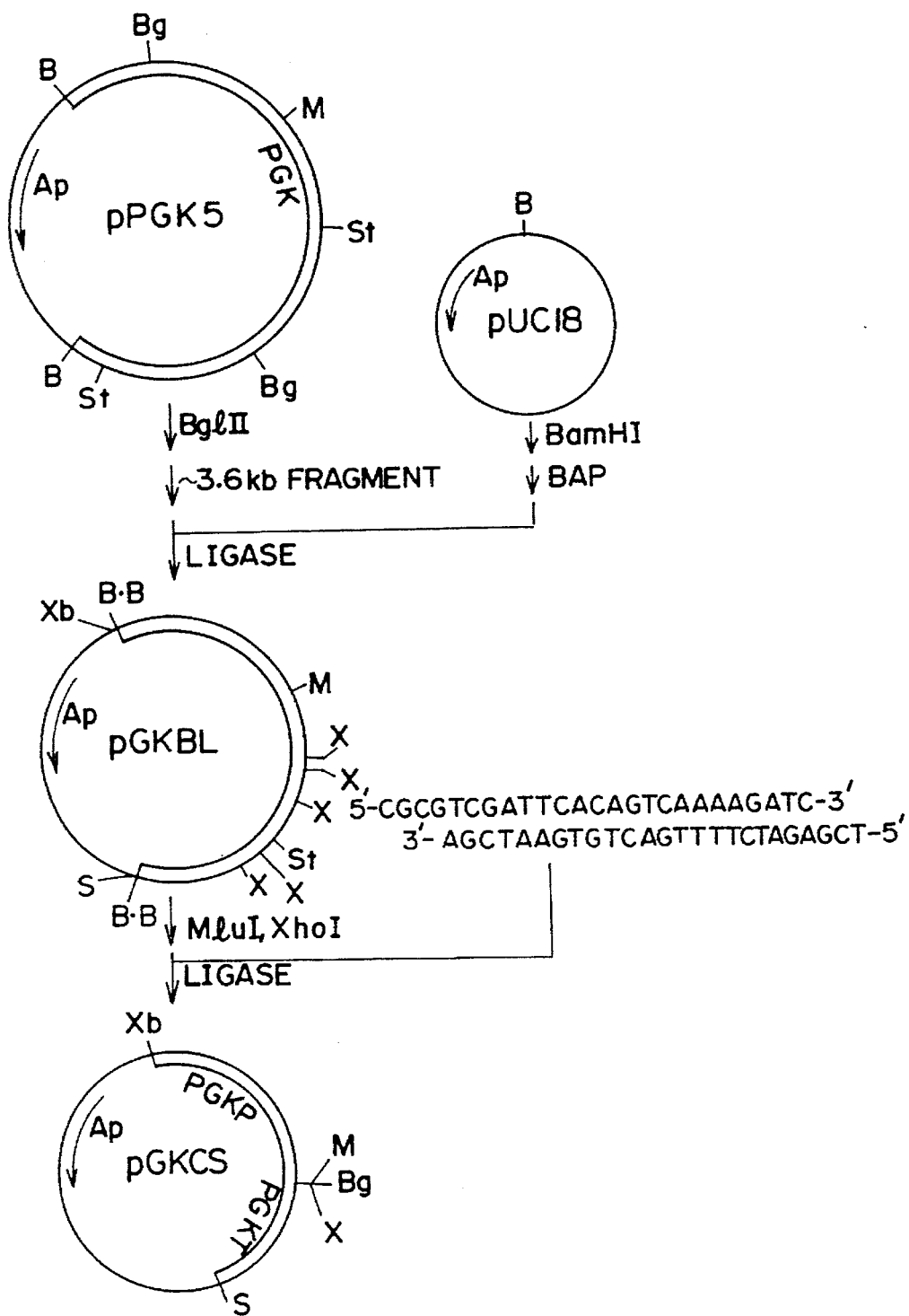
FIG. 12 is a diagram showing a preparation process for plasmid pGKCS.

In accordance with the steps shown in FIG. 8, plasmid pTCATF1 is constructed for use in the expression of DCPC-ATFcDNA in *Acremonium chrysogenum*. Plasmid pCCS1 obtained in Example 1 is digested with EcoRI, and the terminuses of the digested plasmid are rendered blunt by using DNA polymerase large fragment and four types of deoxyribonucleotides. Then the resultant reaction mixture is subjected to agarose gel electrophoresis, and a fragment of about 1.25 kb containing the entire code region of DCPC-ATF is collected from the gel and purified. The purified fragment is ligated, by means of T4 ligase, to pGKCS (see Reference Example 2) (which has been digested with BglII and rendered blunt at the terminuses by means of DNA polymerase large fragment and four types of deoxyribonucleotides and treated with alkaline phosphatase), thereby obtaining pGKATF1.

Subsequently, pGKATF1 is digested with XbaI and SmaI and subjected to agarose gel electrophoresis, and a fragment of about 3.4 kb containing DCPC-ATFcDNA and PGK promoter and terminator is collected from the gel and purified. On the other hand, plasmid pACTHY83 obtained in Reference Example 3 is digested with XbaI and SmaI, and subjected to agarose gel electrophoresis, and a fragment of about 5.8 kb is collected from the gel and purified. The thus obtained XbaI-SmaI fragments of pGKATF1 and pACTHY83 are ligated to each other by means of T4 ligase to thereby obtain pTCATF1.

In the above procedure, operations, such as separation and purification of a DNA fragment obtained by digestion with a restriction enzyme; ligation reaction between DNA fragments to form a plasmid; transformation of *E. coli* by means of the thus obtained plasmid; preparation of a plasmid from the thus obtained transformant; and analysis of the thus prepared plasmid, are performed substantially in accordance with the methods described in Maniatis' Laboratory Manual. Further, it should be noted that plasmid pACTHY83 is a vector for transforming *Acremonium chrysogenum* and contains the hygromycin B phosphotransferase expression unit (in which the promoter and terminator of the actin gene derived from *Acremonium chrysogenum* are linked to the hygromycin B phosphotransferase gene derived from bacteria in a sequence suitable for expression) which can function in *Acremonium chrysogenum*. The method for preparing plasmid pACTHY83 is described in Reference Example 3 of the present application.

III. Transformation of *Acremonium chrysogenum* with pTCATF1

Plasmid pTCATF1 is introduced into *Acremonium chrysogenum* IS-5 strain, to thereby obtain a transformant having an enhanced DCPC-ATF activity. The details of the procedure are described below.

Step (1) Preparation of protoplast

A mycelium obtained by allowing *Acremonium chrysogenum* IS-5 to grow at 30° C. for 5 days on a CM solid medium is inoculated into 50 ml of a CM medium and cultured at 30° C. for 3 days on a rotary shaker (250 rpm). Subsequently, 1 ml of the resultant culture suspension is inoculated into 50 ml of a GAG medium and cultured at 30 ° C. for 20 hours. 50 ml of the culture suspension thus obtained is subjected to centrifugation at 3500 rpm for 10 minutes, to thereby precipitate the mycelium. The mycelium is washed with a 0.9% NaCl solution and suspended in 20ml of McIlvaine buffer (0.1 M citric acid, 0.2 M sodium phosphate, pH7.3) containing 0.01M dithiothreitol and kept at 30° C. for 1 hour while gently shaking. Then, the suspension is subjected to centrifugation at 3200 rpm for 10 minutes, to thereby precipitate the mycelium. The mycelium is washed with P-buffer and suspended in 10 ml of P-buffer containing Novozyme 234 (manufactured and sold by Novo Industry, Denmark) at a concentration of 10 mg/ml, and subjected to gentle shaking at 30° C. for 1 hour. The resultant reaction mixture is subjected to centrifugation at 800 rpm for 30 seconds, thereby to obtain a supernatant. The supernatant is filtered by means of a filter paper (Toyo Filter Paper 5A), to thereby separate the mycelium and the protoplast from each other. The filtrate is then subjected to centrifugation at 3000 rpm for 5 minutes, to precipitate the protoplast, and the protoplast is washed with P-buffer one time and suspended in P-buffer so that the concentration of the protoplast becomes about $3 \times 10^8$/ml.

Step (2) Transformation of protoplast with pTCATF1

To 0.1 ml of the protoplast suspension obtained in Step (1) above is first added 10 µl of a solution containing 10 µg of plasmid pTCATF1 and is then added 0.05 ml of PEG solution, followed by lightly stirring. The resultant mixture is allowed to stand on ice for 25 minutes and then 1 ml of PEG solution is added, followed by being allowed to stand at room temperature for 30 minutes.

The thus obtained transformed protoplast suspension is spread onto a plate containing 25 ml of a protoplast regeneration medium (which is the BRM medium described by Isogai et al: Argic. Biol. Chem. 1987, 51, 2321–2329) in an amount of 0.2ml, followed by incubation at 15° C. for 20 hours. Then, 5ml of BRM medium which contains 4.5 mg of hygromycin B added thereto and is kept at 50° C., is superposed on the above plate, followed by incubation at 28° C. for 14 days. As a result, 70 strains of transformants (hereinafter referred to simply as "HYB transformants") which have been rendered resistant to hygromycin B appear.

Step (3) Measurement of DCPC-ATF activity

From the HYB transformants obtained in Step (2) above using plasmid pTCATF1, 4 strains are selected at random and designated CAT1, CAT2, CAT3 and CAT4, respectively. From the HYB tranformants obtained in Step (2) above using plasmid pACTHY83, 2 strains are selected at random and designated C1 and C2. Each of the above 5 strains is inoculated into 50 ml of N3 seed medium, individually and subjected to shaking (220 rpm) at 25° C. for 3 days. Then, 1 ml of the culture liquid is transferred into a 500 ml flask containing 30 ml of a main medium and subjected to shaking (220rpm) at 25° C. for 3 days. 1 ml of the culture liquid thus obtained is subjected to centrifugation, to collect the cells and the collected cells are suspended in 1 ml of ATF stabilizing buffer and subjected to a treatment with a supersonic crusher to disrupt the cells. The resultant liquid containing disrupted cells is subjected to centrifugation to collect a supernatant as a crude cell extract. 0.05ml of the crude cell extract is mixed with 0.05 ml of 0.2 M Tris-HCl solution (pH7.5) containing 8 mM magnesium sulfate, 10 mM acetyl coenzyme A and 5 mM deacetyl cephalosporin C and reacted at 30° C. for 30 minutes. Then 0.1ml of methanol is added thereto, to terminate the reaction. The resultant reaction mixture is subjected to centrifugation to obtain a supernatant and the supernatant is subjected to high-performance liquid chromatography, to thereby effect the quantitative determination of cephalosporin C as a reaction product, which value, in turn, is used for assessing the DCPC-ATF activity. The chromatography is conducted under conditions such that the column is ZORBAX-BPNH$_2$ column (manufactured and sold by E.I.Du Pont De Nemours and Company, U.S.A.), the mobile phase is a solution containing 4% acetic acid, 4% methanol and 8% acetonitrile, the flow rate is 2 ml/minute and the wavelength for detection is 245 nm. The results are shown in Table 1. As is apparent from Table 1, two of the HYB transformants which have been transformed with plasmid pTCATF1, exhibit DCPC-ATF activities which are 3 to 4 times higher than those of the HYB transformants which have been transformed with plasmid pACTHY83 employed as a control.

TABLE 1

| Cell strain | Plasmid | DCPC-ATF activity |
| --- | --- | --- |
| C1 | pACTHY83 | 3.1 |
| C2 | pACTHY83 | 2.5 |
| CAT1 | pTCATF1 | 11.6 |
| CAT2 | pTCATF1 | 3.8 |
| CAT3 | pTCATF1 | 8.6 |
| CAT4 | pTCATF1 | 2.4 |

Note: The amount of an enzyme which produces cephalosporin C at a rate of 1 nmole per minute is taken as 1 unit, and the number of units per milligram of the protein contained in the crude cell extract is shown in Table 1 as a DCPC-ATF activity.

The above results indicate that by the use of the DNA fragment of the present invention, the DCPC-ATF activity of *Acremonium chrysogenum* can be raised.

EXAMPLE 2

(Production of DNA containing DCPC-ATF genomic DNA)

I. Isolation of DCPC-ATF genomic DNA

Step (1) Preparation of gene library of *Acremonium chrysogenum*

The total DNA of the strain of *Acremonium chrysogenum* IS-5 deposited at Fermentation Research Institute, Japan under accession number FERM BP-11232, is extracted in substantially the same manner as the method for the isolation from *Aspergins nidulans* employed by Johnstone et al. [see I.L. Johnstone, EMBO J. (1985) 4, 1307–1311]. About 60 µg of the total DNA is partially digested with MboI, followed by the treatment of alkaline phosphatase. On the other hand, 10 µg of vector EMBL3 (manufactured and sold by Promega Co., USA) is completely digested with BamHI and EcoRI, and the resultant digested DNA is precipitated by isopropanol to thereby remove the shorter EcoRI-BamHI fragment. Subsequently, about 1 µg of the thus obtained partially digested DNA fragment and about 2 µg of a vector having a terminus produced by BamHI are ligated with T4 ligase to thereby obtain an inserted λ-phage particle. Eschericia coli NM593 (manufactured and sold by Promega Co., USA) is infected with the obtained recombinant phage suspension diluted in an appropriate concentration, followed by measurement of the number of plaques. As a result, $3\times10^5$ recombinant phages are found to be in the suspension. The phage suspension is stored at 4° C. as gene library of *Acremonium chrysogenum*.

Preparation of the above-mentioned donor DNA and vector and the procedure for combining them are in accordance with the method of Frischauf et al. [see J. Mol. Biol. (1983) 170, 827–842]. Introduction of DNA into λparticles is performed using Packaging Extract (manufactured and sold by Promega Co., USA) according to the procedure described in the protocol.

Step (2) Preparation of probe

10 μg of pCCS1 (the preparation of the corresponding plasmid containing cDNA insert coding for DCPC-ATF is described in the Example 1) is digested with EcoRI, and the resultant digested DNA is subjected to 1% agarose gel electrophoresis. A cDNA fragment of 1.25 kb containing the entire code region of DCPC-ATF is recovered from agarose gel by the use of Gene Clean (Gene Clean®, manufactured and sold by Funakoshi Pharmaceutical Co., Ltd., Japan) to thereby obtain purified cDNA fragment. Then, about 50 ng of the thus obtained fragment is labeled with 50 μCi of ($\alpha$-$^{32}$p) deoxycitidinic acid triphosphate by the use of multiprime DNA labeling system (manufactured and sold by Amersham International, England). Subsequently the reaction mixture is heated at 70° C. for 10 min, followed by purification using Nick-column® (manufactured and sold by Pharmacia Fine Chemicals, AB, Sweden) to thereby obtain a probe having a radioactivity of about $10^7$ cpm. Hereinafter, the resultant probe is designated as ATF-probe.

Step (3) Screening by hybridization

E. coli NM539 is infected with an aliquot of the phage suspension (DNA library) obtained in (1) and cultured on four plates of culture medium to thereby form $1.5\times10^4$ plaques. These plaques are transferred to a nitrocellulose filter, and the resultant filter is denatured by alkali and neutralized, followed by fixing of the DNA according to the method by Benton et al. [see Benton W.D., Science (1977) 196, 180–182]. Subsequently, these plaques are hybridized with the ATF-probe obtained in Step (2) above. Hybridization is performed at 42° C. for 15 hr by the use of a solution containing 50% formamide, 5xDenhardt's, 5×SSPE, 0.1% SDS and ATP-probe at a final concentration of $4\times10^5$ cpm/ml. Then the filter is washed twice for 10 min at room temperature with 2×SSC solution containing 0.1% SDS, and further washed for 30 min at 50° C. with 0.2×SSC solution containing 0.1% SDS. Afterward, using an intensifier screen, autoradiography is conducted at −80° C. for 24 hr. As a result, six positive spots are found. Phage is extracted from agar portions corresponding to three spots of the six positive spots and subjected to plaque hybridization according to the method as described above, to thereby obtain three purified positive phage clones. These clones are designated as λ-ATF1, λ-ATF2, and λ-ATF3, respectively.

Step (4) Subcloning of DCPC-ATF gene and determination of location thereof

Figure 3:
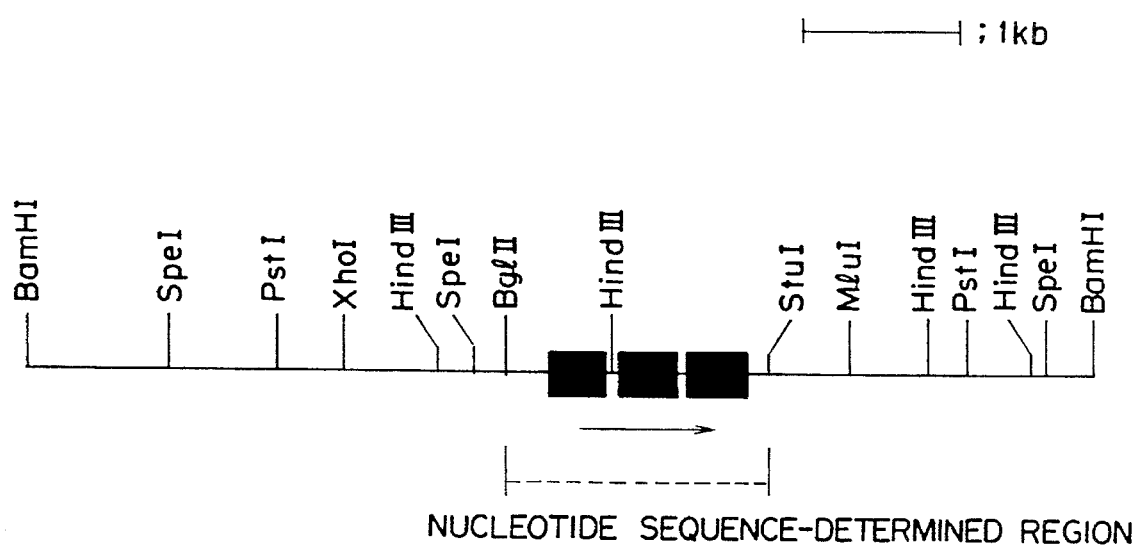
FIG. 3 shows the restriction map of a DNA fragment containing the DCPC-ATF gene of *Acremonium chrysogenum*, wherein the portions marked ■ represent the exons of the DCPC-ATF gene (the 5'-terminus of the first exon and the 3'-terminus of the third exon have not yet been determined) and wherein the mark ⊢---⊣ indicates the region which has been determined with respect to the nucleotide sequence thereof and the arrow ( ——→ ) indicates the orientation of the DCPC-ATF gene.

DNA is extracted from the three types of phage clones obtained in step (3) above according to the method described by Grossberger [see Nucleic Acids Research (1987) 15, 6737]. The resultant λDNA is digested with BamHI, and subjected to agarose gel electrophoresis, followed by the Southern hybridization using ATF-probe [with respect to the method, see Southern, J. Mol. Biol. (1975), 98, 503–517]. Hybridization and washing of the filter are conducted in the same manner as described in step (3) above. As a result, it is found that only the BamHI fragment of about 7 kb which is present in all of the clones can be hybridized with the ATF-probe. This BamHI fragment of about 7 kb is collected from the agarose gel and purified in the same manner as in Step (2) above. On the other hand, plasmid pUC18 for use as a vector is cleaved with BamHI and then treated with alkaline phosphatase. Subsequently, the thus obtained BamHI fragment and the plasmid are ligated to each other by means of T4 ligase and introduced into *E. coli* JM105 and spread on an Lbroth agar medium containing ampicillin (100 μg/ml) and 5-bromo-4-chloro-3-indolyl-β-galactoside (0.004%) in accordance with the method described in the Maniatis Laboratory Manual. From the white colonies obtained by the above procedure, 6 colonies are selected and subjected to extraction of the plasmid DNA by the rapid, small-scale isolation method (described in Maniatis Laboratory Manual), and the thus obtained plasmid DNAs are analyzed through digestion with BamHI. As a result, it is found that the plasmid DNAs of all of the clones have a fragment of the desired length inserted therein. Further, the plasmid DNAs are analyzed by Southern hybridization in the same manner as described above and as a result, it is confirmed that the insert in the clones is the desired fragment. One of the thus obtained plasmids is designated "pATF1". Plasmid pATF1 is digested with various restriction enzymes, and then subjected to agarose gel electrophoresis, thereby obtaining the restriction map of the 7kb insert shown in FIG. 3. Subsequently, in order to determine the location of the region coding for DCPC-ATF, Southern hybridization is performed between each of the fragments obtained by the digestion of pATF1 with various restriction enzymes and the ATF probe. As a result, it is found that the BglII-StuI fragment of about 1.7kb contains a major portion of the region coding for DCPC-ATF.

Step (5) Determination of the nucleotide sequence of the DCPC-ATF gene

The entire nucleotide sequence of the above-mentioned BglII-StuI fragment is determined by the method of Sanger et al. Illustratively stated, the operation is performed by using a sequencing kit (manufactured and sold by Takara Shuzo Co., Ltd., Japan) in accordance with the protocol attached to the kit. After the determination of the nucleotide sequence, the nucleotide sequence is compared with the nucleotide sequence of the DCPC-ATF·cDNA which is already known [see FIG. 2 (A) and (B)]. As a result, it is found that the nucleotide sequence determined above comprises the nucleotide sequence of the DCPC-ATF·cDNA. Thus, it is confirmed that the BglII-StuI fragment contains the entire region coding for DCPC-ATF. It is also found that the DCPC-ATF gene comprises at least two introns and at least three exons. The nucleotide sequence of 1731bp determined above is shown in FIG. 4 together with the amino acid sequence of a translation product thereof.

II. Construction of plasmid pTATF1

Figure 5:
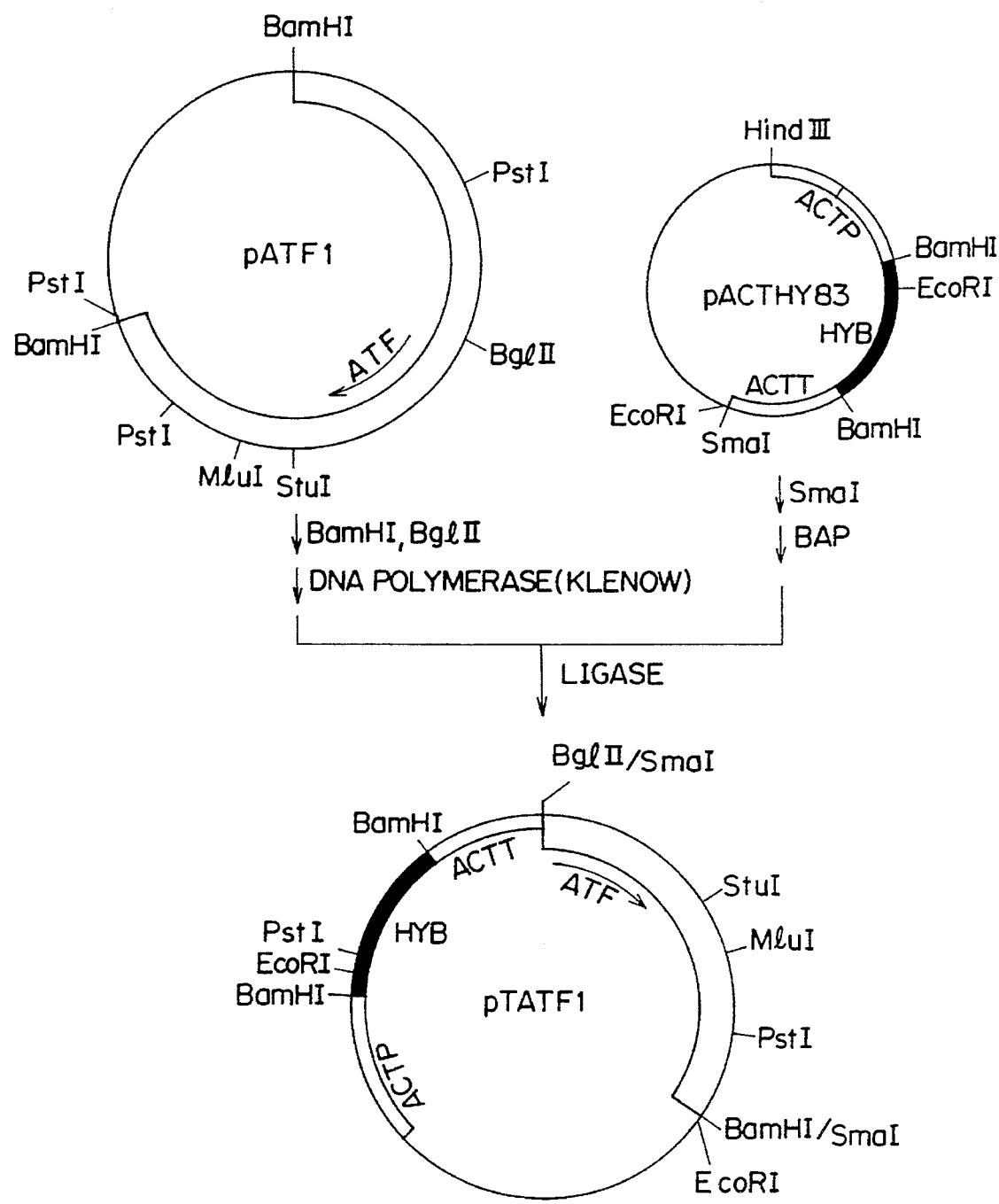
FIG. 5 is a diagram showing the process for the production of plasmid pTATF1.

In accordance with the steps shown in FIG. 5, plasmid pTATF1 is constructed for use in the introduction of the additional copy of the DCPC-ATF gene into *Acremonium chrysogenum*. Hereinbelow, the steps are described. First, plasmid pATF1 obtained in Step (4) of Example 2 is digested with both BglII and BamHI, simultaneously, and then reacted with DNA polymerase Klenow fragment and four types of deoxynucleotide triphosphates, to thereby render blunt the ends formed by the digestion. Then the resultant reaction mixture is subjected to agarose gel electrophoresis and a fragment of about 3.8 kb containing the entire region coding for DCPC-ATF is collected from the gel and purified. The thus obtained fragment is ligated, by means of T4 ligase, to pACTHY83 which has been cleaved by SmaI and treated with alkaline phosphatase, to thereby obtain plasmid pTATF1. In the above procedure, operations, such as separation and purification of a DNA fragment obtained by digestion with a restriction enzyme; ligation reaction between DNA fragments to form a plasmid; transformation of E. coli by means of the thus obtained plasmid; preparation of a plasmid from the thus obtained transformant; and analysis of the thus prepared plasmid, are performed in the same manner as in section I of Example 1 and in accordance with the methods described in the Maniatis Laboratory Manual.

III. Transformation of Acremonium chrysogenum with pTATF1

Plasmid pTATF1 is introduced into Acremonium chrysogenum IS-5 strain, to thereby obtain a transformant having an enhanced ability to synthesize DCPC-ATF. The details of the procedure are described below.

Step (1) Transformation of protoplast with pTATF1

To 0.1 ml of the protoplast suspension obtained in the same manner as in Example 1 is first added 5 μg (10 μl) of plasmid pTATF1 and is then added 0.05 ml of PEG solution, followed by gentle stirring. The resultant mixture is allowed to stand on ice for 25 minutes and then 1 ml of PEG solution is added, followed by being allowed to stand at room temperature for 30 minutes. The thus obtained transformed protoplast suspension is spread in the form of spots onto a plate containing 25 ml of a protoplast regeneration medium (which is the BRM medium described by Isogai et al: Argic. Biol. Chem. 1987, 51, 2321–2329) in an amount of 0.2 ml per spot, followed by incubation at 15° C. for 20 hours. Then, 5ml of the BRM medium which contains 4.5 mg of hygromycin B added thereto and is kept at 50° C., is superposed on the above plate, followed by incubation at 28° C. for 14 days. As a result, 60 strains of transformants (hereinafter referred to simply as "HYB transformants") which have been rendered resistant to hygromycin B appear. Using plasmid pACTHY83 as a control plasmid, substantially the same transformation as described above is conducted, thereby obtaining 75 strains of HYB transformants.

Step (2) Measurement of DCPC-ATF activity

From the HYB transformants obtained using plasmid pTATF1 in Step (2) above, 3 strains are selected at random and designated as AT1, AT2 and AT3. From the HYB tranformants obtained using plasmid pACTHY83 in Step (2) above, 2 strains are selected at random and designated as C1 and C2. Each of the above 5 strains is individually inoculated into 50 ml of N3 seed medium and subjected to shaking (220 rpm) at 25° C. for 3 days. Then, 1 ml of the culture liquid is transferred into a 500 ml flask containing 30 ml of a main medium and subjected to shaking (220 rpm) at 25° C. for 3 days. 1 ml of the culture liquid thus obtained is subjected to centrifugation, to collect the cells and the collected cells are suspended in 1 ml of ATF stabilizing buffer and subjected to a supersonic crusher, to disrupt the cells. The ATF activity in the resultant liquid containing disrupted cells is measured by the method described in Example 1. The results are shown in Table 2. As is apparent from Table 2, the HYB transformants which have been transformed with plasmid pTATF1, exhibit DCPC-ATF activities which are 3 to 4 times higher than those of the HYB transformants which have been transformed with plasmid pACTHY83 employed as a control.

TABLE 2

| Cell strain | Plasmid | DCPC-ATF activity |
| --- | --- | --- |
| C1 | pACTHY83 | 3.1 |
| C2 | pACTHY83 | 2.5 |
| AT1 | pTATF1 | 9.4 |
| AT2 | pTATF1 | 8.4 |
| AT3 | pTATF1 | 9.7 |

Note: The amount of an enzyme which produces cephalosporin C at a rate of 1 nmole per minute is taken as 1 unit, and the number of units per milligram of the protein contained in the crude cell extract is shown in Table 2 as a DCPC-ATF activity.

The above results indicate that by the use of the DNA fragment of the present invention, the DCPC-ATF activity of Acremonium chrysogenum can be raised. Further, the above results also suggest that the DNA fragment of the present invention which is the BglII-BamHI fragment of 3.8 kb contains the promoter and terminator of the DCPC-ATF gene.

Reference Example 1

[Isolation of deacetylcephalosporin C acetyltransferase]

The methods for measurement employed in Reference Examples are as follows.

[Method 1] Measurement of enzyme activity

The activity of DCPC-ATF is measured by effecting reaction using as substrates deacetylcephalosporin C and acetyl-coenzyme A to produce cephalosporin C, determining the cephalosporin C by high performance liquid chromatography and calculating the activity based on the amount of the produced cephalosporin C. Illustratively stated, measurement of the activity is conducted as follows.

To 0.1 ml of 1M Tris-HCL (pH7.5) containing 4 mM magnesium sulfate, 2.5 mM deacetylcephalosporin C and 5 mM acetyl-coenzyme A is added the enzyme in an amount of 0.0001 to 0.001U and the resultant mixture is reacted at 30° C. for 30 minutes, followed by adding 0.1 ml of ethanol to terminate the reaction. The resultant reaction mixture is subjected to centrifugation (10,000 ×g) for 2 minutes, to obtain a supernatant. The formed cephalosporin C contained in the supernatant is determined by high performance liquid chromatography, under conditions such that the column is ZORBAX-BP NH2 column (manufactured and sold by E.I.Du Pont De Nemours and Company, U.S.A; 4.5 M mm ×25 cm), the mobile phase is a solution containing 4% acetic acid, 4% methanol, acetonitrile and 84% water, the flow rate is 1.5 to 2.2 ml/minute, and the wavelength for measurement is 254 nm. As an external standard, a standard product of cephalosporin C is employed.

[Method 2] Measurement of molecular weight

The molecular weight of active DCPC-ATF is calculated by gel filtration using TSK gel G3000SWXL (manufactured and sold by Toyo Soda Mfg.Co., Ltd., Japan; 7.8 mm ×30 cm). As the molecular weight standard, bovine serum albumin (molecular weight: 67000), ovalbumin (molecular weight: 43000), chymotrypsinogen A (molecular weight: 25000) and ribonuclease A (molecular weight: 13700) are employed.

The molecular weight of each subunit is measured by SDS polyacrylamide gel electrophoresis. As the molecular weight standard, phospholipase B (molecular weight: 94000), bovine serum albumin (molecular weight; 67000), ovalbumin (molecular weight: 43000), carbonic anhydrase (molecular weight: 30000), soybean trypsin inhibitor (molecular weight: 20100) and α-lactalbumin (molecular weight: 14400) are employed.

[Method 3] Measurement of protein concentration

The protein concentration is measured using bovine serum albumin as a standard in accordance with the method of Bradford, M.M., Analytical Biochemistry, 72, 248 to 254 (1976).

[Method 4] Analysis of amino acid sequence

An amino acid sequence is analyzed by a method in which purified DCPC-ATF is separated into two subunits by SDS polyacrylamide gel electrophoresis, followed by extracting the subunits from the gel and the subunits are individually subjected to Edman degradation reaction under customary conditions and the amount of phenylthiohydantoin amino acid derivative obtained in each cycle is determined.

The determination of the phenylthiohydantoin amino acid derivative is conducted under conditions such that the column is PTH-C18 (manufactured and sold by Applied Biosystems, U.S.A.) and the wavelength for detection is 269 nm.

[Purification of DCPC-ATF]

*Acremonium chrysogenum* is cultured in a medium comprising 2% of saccharose, 0.5% of calcium carbonate, 0.8% of ammonium acetate, 3% of starch, 5% of molasses, 6% of de-fatted soybean and 3% (pH6.4) of methyl oleate. The resultant cultured broth is subjected to centrifugation (6000 ×g) for 10 minutes to collect cells and the cells are washed with 50 mM phosphate buffer (pH7.0) containing 0.85% sodium chloride, to thereby obtain a wet preparation of cells.

500 g of the above-obtained wet preparation of cells is suspended in 50 mM phosphate buffer (pH7.0) containing 15% ethylene glycol, 10 mM dithiothreitol, 10 mM 7-aminocephalosporanic acid, 1 mM EDTA and 1 mM paraaminodiphenylmethanesulfonyl fluoride hydrochloride, to a total volume of 1 liter. The subsequent operation is conducted at 5° C. The above suspension of cells is subjected to ultrasonic treatment and then subjected to centrifugation at 15000 ×g for 10 minutes, to obtain a supernatant fraction as a crude enzyme liquid. It is found that the crude enzyme liquid has a total protein of 22.9 g and a total activity of 25.7 U and a relative activity of 0.001U/mg. [The amount of an enzyme which produces cephalosporin C at a rate of 1 µmole per minute is taken as 1 unit, and the number of units per milligram of the protein contained in the crude cell extract is taken as a DCPC-ATF specific activity.]

One-fourth volume of the crude enzyme liquid is adsorbed onto DEAE-Sepharose CL-6B column (4 cm ×50 cm; manufactured and sold by Pharmacia Fine chemical AB, Sweden) which has been equilibrated with phosphate buffer containing ATF-BASE, and elution is conducted at a flow rate of 200 ml/hour using a linear gradient of 0 to 0.5 M sodium chloride in an ATF-stabilizing buffer (total volume: 2500 ml). DCPC-ATF fraction is eluted when the concentration of sodium chloride is in the range of 0.17 to 0.2 M. The above procedure is conducted 4 times to thereby treat the whole volume of the crude enzyme liquid. By the above described weakly basic anion exchange chromatography, a DCPC-ATF fraction having a total protein of 800 mg, a total activity of 7.1U and a relative activity of 0.009 U/mg is obtained.

To the above-obtained DCPC-ATF active fraction is added ammonium sulfate in an amount such that 25% saturation is attained, and stirred for 15 minutes while cooling, to dissolve the ammonium sulfate. The DCPC-ATF active fraction is adsorbed onto Phenyl-Sepharose CL-4B column (3 cm ×20 cm, manufactured and sold by Pharmacia Fine chemicals AB, Sweden) which have been equilibrated with an ATF stabilizing buffer. Elution is conducted under conditions such that a linear gradient of 25 to 0% ammonium sulfate and 10 to 60% ethylene glycol in an ATF stabilizing buffer is employed, the flow rate is 150 ml/hour and the total volume is 1000 ml. The DCPC-ATF active fraction is eluted when the ammonium sulfate concentration is 8 to 3% and the ethylene glycol concentration is 40 to 48%. Thus, a DCPC-ATF fraction having a total protein of 16 mg and a total activity of 1.9 U and a relative activity of 0.12 U/mg is obtained. The DCPC-ATF active fraction is concentrated so that the total volume becomes 6 ml, by means of Centriprep 10 (manufactured and sold by Amicon Plastics Inc. U.S.A.). One-third volume of the concentrated solution is packed into Sephacryl S-200 Superfine Column (4 cm ×80 cm; manufactured and sold by Pharmacia Fine Chemicals AB, Sweden) which has been equilibrated with an ATF stabilizing buffer, and gel filtration is conducted 3 times at a flow rate of 40 ml/hour. Thus a DCPC-ATF fraction having a total protein of 2 mg and a total activity of 0.4 U and a relative activity of 0.2 U/mg is obtained.

The above-obtained DCPC-ATF fraction is concentrated so that the total volume becomes 2 ml, by means of Centriprep 10 (manufactured and sold by Amicon Plastics Inc., U.S.A.). The concentrated solution is adsorbed onto TSK-gel DEAE-5PW (which is a column for high performance liquid chromatography for purifying protein) (2.1 cm ×15 cm; manufactured and sold by Toyo Soda Mfg. Co., Ltd., Japan) which has been equilibrated with an ATF stabilizing phosphate buffer. Elution is conducted under conditions such that a linear gradient of 0 to 0.5 M sodium chloride in an ATF stabilizing buffer is employed, the flow rate is 3 ml/minute and the total volume is 300 ml. Thus a purified DCPC-ATF enzyme having a total protein of 0.1 mg and a total activity of 0.13 U and a relative activity of 1.3 U/mg and a purity of about 100% is obtained. The results of each stage of the above described procedure for purifying the enzyme are summarized in Table 3 below.

TABLE 3

| Stage | Total protein (mg) | Total activity (unit) | Active yield (%) | Specific activity (U/mg) | Purification degree (times) |
|---|---|---|---|---|---|
| Crude enzyme liquid | 22900 | 25.7 | 100 | 0.001 | 1 |
| Weakly basic anion exchange chromatography (1st stage) | 800 | 7.1 | 28 | 0.009 | 8 |
| Hydrophobic chromatography (2nd stage) | 16 | 1.9 | 7 | 0.12 | 120 |
| Gel filtration (3rd stage) | 2 | 0.4 | 1.6 | 0.2 | 200 |
| Weakly basic anion exchange HPLC (4th stage) | 0.1 | 0.13 | 0.5 | 1.3 | 1300 |

Note: "HPLC" means high performance liquid chromatography The chart obtained at each stage is shown in FIGS. 9–12.

The thus obtained purified enzyme is investigated with respect to its characteristics. The results are shown in items a to f below.

a. The enzyme is separated into two subunits 1 and 2 by SDS polyacrylamide gel electrophoresis. Subunit 1 has a molecular weight of 27,000±2,000 dalton and Subunit 2 has a molecular weight of 14,000±2,000 dalton.

b. The enzyme has a molecular weight of 55,000±2,000 dalton as measured by gel filtration.

c. The enzyme has an isoelectric point at pH4.0±0.5 d. Subunit 1 has the following amino acid sequence (Seq. ID No. 6) at the N-terminus:

Leu—X—Ala—Gln—Asp—Ile—Ala—Arg—Ile—Ser—Leu—Phe—Thr—Leu—
Glu—Ser—Gly—Val—Ile—Leu—Arg, wherein X means a portion which cannot be determined.

e. Subunit 2 has the following amino acid sequence (Seq. ID No. 7) at the N-terminus:

Asp—Ser—Gly—Asn—Ser—His—Arg—Ala—Gly—Gln—Pro—Ile—Glu—
Ala—Val—Ser—Ser—Tyr—Leu—Arg—Tyr—Gln—Ala—Gln—Lys—Phe—Ala

Reference Example 2 [Construction of pGKCS]

I. Isolation of *Acremonium chrysogenum* phosphoglycerate kinase (PGK) gene

Step (1) Preparation of gene library of *Acremonium chrysogenum*

The total DNA of *Acremonium chrysogenum* IS-5 strain (deposited at Fermentation Research Institute, Japan under the accession number FERM BP-11232) is extracted according to the method employed by Johnstone et al with respect to Aspergillus nidulans (see I.L. Johnstone et al, EMBO J., 4, 1307–1311, 1985). About 60 μg of the total DNA is partially digested with restriction enzyme MboI, and then treated with alkaline phosphatase. On the other hand, 10 μg of lambda-vector EMBL3 (manufactured and sold by Promega Co., USA) is completely digested with BamHI and EcoRI and subjected to isopropanol precipitation, to thereby remove the short linker EcoRI-BamHI fragment. Next, about 1 μg of the above-obtained partially digested DNA fragment is subjected to ligation reaction with 2 μg of the vector having a BamHI terminus by the use of T4 ligase, followed by packaging into a lambda-phage particle. The thus obtained recombinant phage suspension obtained is diluted to an appropriate concentration, and used for infecting *Escherichia coli* NM539 (manufactured and sold by Promega Co., USA) to form plaques, and the number of plaques formed is counted. As a result, it is found that the phage suspension contains $3 \times 10^5$ particles of the recombinant phage. This phage suspension is stored at 4° C. as a gene library of *Acremonium chrysogenum*. In the above procedure, the preparation of the donor DNA and the vector, and the ligation reaction therebetween are conducted by the methods described by Frischauf et al (J. Mol. Biol., 170, 827–842, 1983). In addition, the packaging of the DNA into the lambdaparticle is performed by using Packaging extract (manufactured and sold by Promega Co., USA) in accordance with protocol attached to the same.

Step (2) Preparation of probe

The total DNA of *Saccharomyces cerevisiae* is digested with HindIII and inserted into the HindIII site of PBR327 (ATCC 37516), to thereby obtain a gene library. The gene library is screened by the synthetic oligonucleotide of the sequence (Seq. ID No. 10): 5'-CAGATCATCAAGAAG-TAATTATCT-3' which has been designed based on the nucleotide sequence of the *Saccharomyces* PGK gene reported by Hitzeman et al (see Nucleic Acids Res., 10, 7791–7808, 1982), to thereby obtain plasmid pYPGK1 which contains a HindIII fragment of 2.9 kb containing the entire PGK gene derived from *Saccharomyces cerevisiae*. 20 μg of plasmid pYPGK1 is digested with HindIII and EcoRI and subjected to 1% agarose gel electrophoresis, followed by the collection and purification of a fragment of 2.9 kb according to the method described at p.164–165 of the Maniatis Laboratory Manual. About 200 ng of the thus obtained fragment is labeled with [α-$^{32}$P] deoxycytidinetriphosphate (dCTP) (50 μCi) by using Nick translation kit (manufactured and sold by Takara Shuzo Co., Ltd., Japan) in accordance with the protocol attached to the same. After heating the reaction mixture at 70° C. for 10 minutes, the labeled fragment is purified by Nick-column (manufactured and sold by Pharmacia Fine Chemicals AB, Sweden), to thereby obtain a probe having a radioactivity of about $10^7$ cpm (hereinafter this probe is referred to as "YP-probe").

Step (3) Screening by hybridization

*E. coli* NM539 is infected with an aliquot of the phage suspension (gene library) obtained in Step (1) above and the infected NM539 is cultured on the four plates to form a total of $2 \times 10^4$ plaques. According to the method of Benton et al (see W.D. Benton et al., Science, 196, 180–182, 1977), these plaques are transferred onto a nitrocellulose filter, followed by denaturation with alkali and neutralization treatment, thereby fixing the DNA. Then, these plaques are hybridized with YP-probe obtained in Step (2) above. Hybridization is performed at 42° C. for 16 hours in a solution containing 30% formamide, 5×Denhardt's, 5×SSPE, 0.1% SDS, and YP-probe at a final concentration of $5 \times 10^5$ cpm/ml. Then, the filter is washed twice in a 6×SSC solution containing 0.1% SDS at room temperature for 10 minutes, followed by washing in 1×SSC solution containing 0.1% SDS at 42° C. for 30 minutes. Next, using an intensifier screen, autoradiography is carried out at −80° C. for 16 hours. As a result, seven positive spots are found. The phage is collected from agar portions corresponding to four of these seven positive spots, and subjected to plaque hybridization in the same manner as described above, to thereby obtain four pure positive phage clones. These clones are designated λ-PGK1, λ-PGK2, λ-PGK3, and λ-PGK4, respectively.

Step (4) Subcloning of PGK gene and the determination of the location

From the four phage clones obtained in Step (3) above, DNA is extracted by the method described by Grossberger (see Nucleic Acids Research, 15, 6737). Then the lambda-DNA is digested with BamHI and then subjected to agarose gel electrophoresis, followed by Southern hybridization using YP-probe (with respect to the method, see Southern, J. Mol. Biol., 98, 503–517, 1975). In the above procedure, hybridization and washing of the filter are conducted in the same manner as in Step (3). As a result, it is found that only the BamHI fragment of about 5.5 kb which is present in all clones is hybridized with the above mentioned YP-probe. The fragment is collected from the agarose gel and purified by the use of Gene·Clean® (manufactured and sold by Funakoshi Pharmaceutical Co., Ltd., Japan) according to the protocol attached to the same. On the other hand, pUC18 (manufactured and sold by Takara Shuzo Co., Ltd., Japan) for use as a vector is digested with BamHI, followed by alkaline phosphatase treatment. Then, the above fragment and the vector are ligated to each other by means of T4 ligase, and introduced into *E. coli* JM105 according to the method described at p.252–253 of Maniatis Laboratory Manual. The resultant transformant is cultured on a L-broth agar medium containing ampicillin (Amp) (100 μg/ml) and 5-bromo-4-chloro-3-indolyl-μ-galactoside (X-Gal) (0.004%), thereby obtaining white colonies. 6 colonies are selected therefrom and subjected to extraction of the plasmid DNA by the rapid, small-scale isolation method (described at p.368–369 of Maniatis Laboratory Manual), and the thus obtained plasmid DNAs are analyzed through digestion with BamHI. As a result, it is found that the plasmid DNAs of 5 clones of the 6 clones have the desired fragment inserted therein. Further, the plasmid DNAs are analyzed by the Southern hybridization in the same manner as described above and as a result, it is confirmed that the insert in the clones is the desired fragment. One of the thus obtained plasmids is designated as "pPGK5".

Plasmid pPGK5 is digested with various restriction enzymes, and then subjected to agarose gel electrophoresis, thereby obtaining the restriction map of the 5.5 kb insert shown in FIG. 6.

Step (5) Preparation of pGKBL

Plasmid pPGK5 obtained in Step (4) above is digested with BglII and a fragment of 3.6 kb containing PGK gene is isolated and purified. The fragment is inserted to the BamHI site of pUC18 prepared in Step (4) above, thereby obtaining pGKBL. At the same time, another plasmid in which the same fragment as mentioned above is inserted in the reverse orientation relative to the case of pGKBL, is also obtained, and the plasmid is designated pGKBL'.

Step (6) Preparation of pGKCS

Plasmid pGKBL obtained in Step (5) above is cleaved with MluI and XhoI, and a fragment of 4.8 kb is isolated and purified. The fragment is ligated to a synthetic linker represented by the following formula (Seq. ID No. 11), thereby obtaining pGKCS:

5' CGCGTCGATTCACAGTCAAAAGATC-3'
3' AGCTAAGTGTCAGTTTTCTAGAGCT-5'

Further, substantially the same operation as mentioned above is conducted except that pGKBL' is used instead of pGKBL, thereby constructing pGKCS'. pGKCS and pGKCS' are plasmids having a structure where fragments containing PGK promoter and terminator derived from *Acremonium chrysogenUm* are inserted through unique restriction sites (BglII and XhoI) in a sequence suitable for expression, and these plasmids are useful as starting materials for constructing vectors for the expression of various types of foreign genes in *Acremonium chrysogenum*. The above-mentioned linker is synthesized as two single strands using DNA synthesizer model 380-A manufactured and sold by Applied Biosystems, according to the conventional method.

Reference Example 3 [Construction of pACTHY83]

I. Cloning of actin gene

Step (1) Screening of clone containing actin gene by hybridization

Using as a probe (hereinafter referred to as "ACT probe") HindI 400 bp fragment (manufactured and sold by Wako Pure Chemical Industries Ltd., Japan) containing the third exon of the human μ-actin gene labeled with $^{32}$p, the gene library of *Acremonium chrysogenum* prepared in Step (1) of Reference Example 2 is screened under the same conditions as in Step (1) of Reference Example 2, thereby obtaining four phages which can be hybridized with the above probe.

Step (2) Subcloning of actin gene and determination of location thereof

DNA is extracted from one of the phages obtained in Step (1) above, and designated as μACT5. Next, μACT5 is digested with XhoI and SalI individually, and subjected to agarose gel electrophoresis, followed by Southern hybridization using the above ACT probe. As a result, it is found that a XhoI fragment of 5.4 kb and two types of SalI fragments having sizes of 1.3 kb and 1.5 kb are hybridized with the probe. Then, these three types of fragments (XhoI-5.4 kb fragment, SalI 1.5 kb fragment and SalI-1.3 kb fragment) are individually subcloned to the SalI site of pUC18, to thereby obtain pACT5X, pACT5SS and pACT5SL. Next, partial restriction maps of these plasmids are prepared, and by overlapping these maps on each other, the partial restriction map of a DNA fragment of about 6 kb which is considered to contain the actin gene, is prepared, as shown in FIG. 13.

The above Southern hybridization is carried out under the same conditions as in Step (4) of Reference Example 2 except that use is made of ACT probe.

II. Construction of pACTHY83

Figure 14:
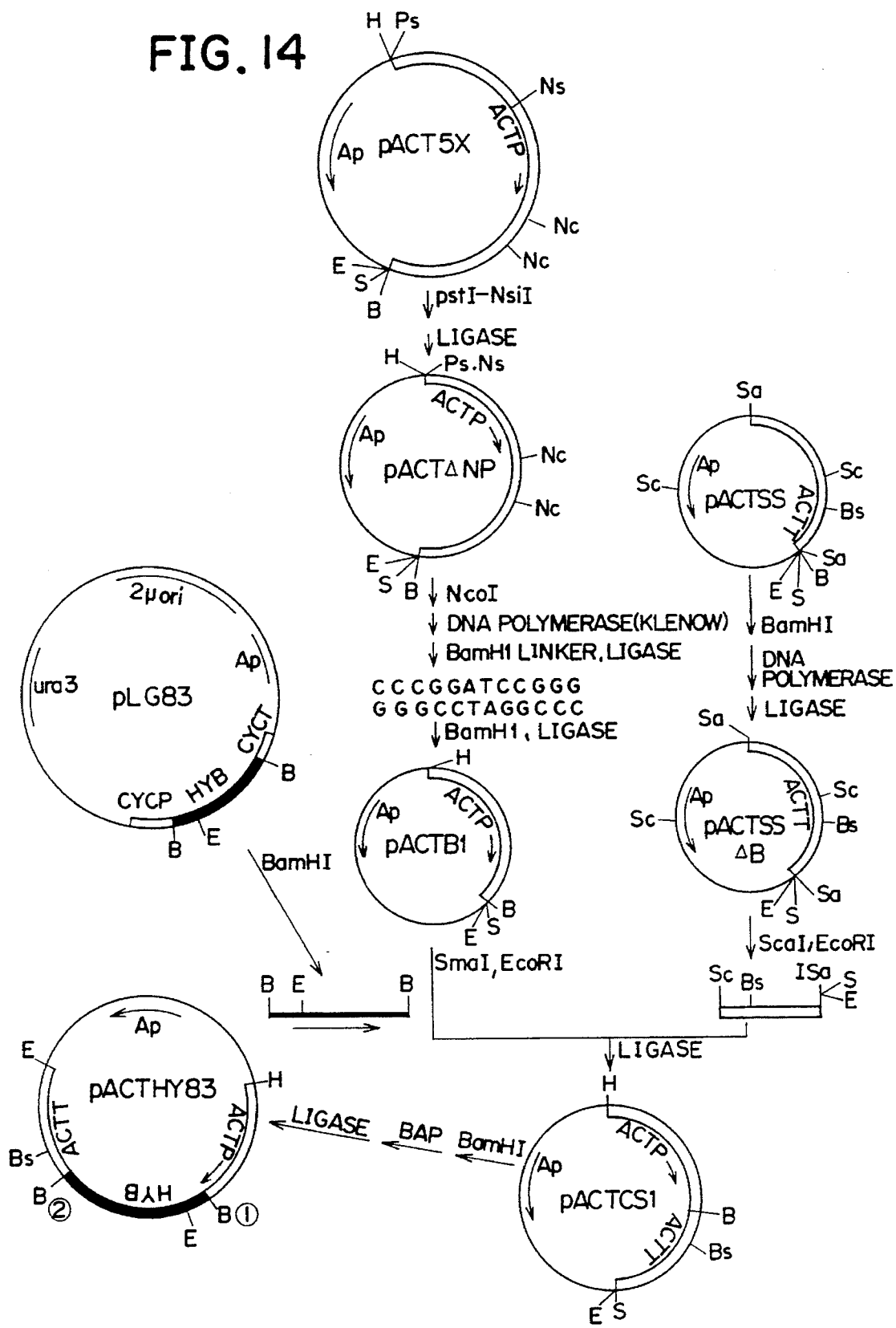
FIG. 14 is a diagram showing a preparation process for plasmid pACTHY83.

According to the steps shown in FIG. 14, plasmid pACTHY83 is constructed for the expression of hygromycin B phosphotransferase gene (hereinafter referred to as "HYB$^R$ gene") under the control of an actin promoter derived from *Acremonium chrysogenum*. Each step is explained as follows.

Step (1) Preparation of pACTΔNP

Plasmid pACT5X obtained in Step (2) of section I above is digested with NsiI and PstI simultaneously, to thereby prepare a fragment of 5.3 kb. Next, the fragment is subjected to re-ligation (self-cyclization) using T4 ligase, to thereby obtain pACTΔNP.

Step (2) Preparation of pACTB1, pACTB2 and pACTB3 pACTΔNP obtained in Step (1) above is digested with NcoI, and the resultant sticky ends are rendered blunt using DNA polymerase Klenow fragment (hereinafter referred to as "DNA pol.") and 4 types of deoxynucleotide triphosphates (deoxyadenosine triphosphate, deoxyguanosine triphosphate, deoxycytidine triphosphate and thymidine triphosphate, which are hereinafter referred to as "4dNTPS"). Then, 5'-terminus is phosphorylated, and a BamHI linker (manufactured and sold by Takara Shuzo Co., Ltd., Japan) having the following sequence (Seq. ID No. 12):

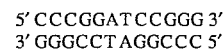
5' CCCGGATCCGGG 3'
3' GGGCCTAGGCCC 5' is ligated to the terminus by means of T4 ligase, followed by digestion with BamHI. The digested product is subjected to agarose gel electrophoresis, and a DNA fragment of 4 kb is isolated and purified. Further the fragment is subjected to self-cyclization using T4 ligase, to thereby obtain pACTB1. Further, using the following two types of BamHI linkers which have different sequences and different numbers of base pair from the above linker, individually:

5' CCGGATCCGG 3'   (Seq. ID No. 13)
3' GGCCTAGGCC 5'

-continued
and

5' CGGATCCG 3'  (Seq. ID No. 14)
3' GCCTAGGC 5'

(both are manufactured and sold by Takara Shuzo Co., Ltd., Japan), the same operation as described above is carried out, to thereby obtain pACTB2 and pACTB3, respectively.

Step (3) Preparation of pACTCS1, pACTCS2 and pACTCS3

Plasmid pACTSS obtained in Step (2) of section I above is digested with BamHI, and the terminuses thereof are rendered blunt using DNA pol. and 4dNTPS, followed by self-cyclization with T4 ligase, to thereby obtain plasmid pACTSSABam which lacks the BamHI site. Then, the plasmid is digested with ScaI and EcoRI, and a fragment of 0.9 kb which is considered to contain the terminator of the actin gene, is isolated and purified. Then the fragment is inserted between the SmaI and EcoRI sites of pACTB1, to thereby obtain pACTCS1. Further, the same fragment of 0.9 kb as mentioned above is inserted between the SmaI and EcoRI sites of each pACTB2 and pACTB3, to thereby obtain pACTCS2 and pACTCS3, respectively. These 3 types of plasmids have a structure where fragments respectively containing an actin promoter and a terminator derived from *Acremonium chrysogenum* are inserted through a unique restriction site BamHI (positioned just downstream of the actin start codon ATG) in a sequence suitable for expression, and the plasmids are useful as starting materials for constructing vectors for expression of various desires genes in *Acremonium chrysogenum* to produce fused proteins. By using one of the three plasmids, desired genes can be ligated in the same reading frame as that of the actin gene.

Step (4) Production of pACTHY83

Plasmid pLG83 (obtained from Prof. Julian Davies of Pasteur Laboratory) is cleaved with BamHI, and a fragment of 1.3 kb containing $HYB^R$ gene is isolated and purified. The fragment is digested with BamHI, and ligated to pACTCS1, which has been subjected to alkaline phosphatase treatment, in the orientation shown in FIG. 14, to thereby obtain pACTHY83. The above mentioned pLG83 is a vector for yeast having $HYB^R$ gene, and characteristics thereof are described in published literature [Gritz et al, Gene (1983) 25. 179–188]. In Steps (1) to (4) above, the basic operations such as isolation and purification of a restriction enzyme-digested fragment, ligation of a plasmid to the fragment, transformation of *E. coli.*, and preparation and analysis of the plasmid obtained by subcloning, are all carried out in the same manner as in section I of Reference Example 2.

What is claimed is:

1. An isolated DNA consisting of a gene coding for deacetylcephalosporin C acetyltransferase from *Acremonium chrysogenum.*

2. The DNA according to claim 1, wherein said gene is a cDNA.

3. The DNA according to claim 1, wherein said gene is a genomic DNA.

4. The DNA according to claim 3, wherein said genomic DNA is defined by a restriction map of FIG. 3 hereof.

5. The DNA according to claim 4, wherein the nucleotide sequence between BglII and StuI indicated in FIG. 3 hereof is as shown in FIG. 4(a)–(b) hereof (Seq. ID No. 3).

6. The DNA according to claim 2, wherein said cDNA is a cDNA encoding aprotein which consists of an amino acid sequence represented by SEQ ID NO: 4.

7. The DNA of claim 6, wherein said cDNA consists of a nucleotide sequence represented by SEQ ID NO: 5, or comprises a nucleotide sequence which is obtained by substituting at least one nucleotide of said nucleotide sequence of SEQ ID NO:5 in accordance with the degeneracy of the genetic code.

8. A recombinant DNA which replicates in a host cell, which consists of a vector having inserted therein the DNA of claim 2, 6 or 7, said DNA coding for a protein having an activity to acetylate deacetylcephalosporin C into cephalosporin C, said recombinant DNA being in a form such that said DNA is expressed in *Acremonium chrysogenum*.

9. *Acremonium chrysogenum* transformed with the recombinant DNA of claim 8.

10. A recombinant DNA which replicates in a host cell, which consists of a vector having inserted therein the DNA of claim 3, 4 or 5, said DNA coding for a protein having an activity to acetylate deacetylcephalosporin C into cephalosporin C, said recombinant DNA being in a form such that said DNA is expressed in *Acremonium chrysogenum*.

11. *Acremonium chrysogenum* transformed with the recombinant DNA of claim 10.

* * * * *

SEQUENCE LISTING ( 1 ) GENERAL INFORMATION:

( i ) APPLICANT: Matsuda, Akio
                              Matsuyama, Kenji ( i i ) TITLE OF INVENTION: AN ACETYLTRANSFERASE GENE-CONTAINING DNA ( i i i ) NUMBER OF SEQUENCES: 14

( 2 ) INFORMATION FOR SEQ ID NO:1:

( i ) SEQUENCE CHARACTERISTICS:
            ( A ) LENGTH: 1261 base pairs
            ( B ) TYPE: nucleic acid
            ( C ) STRANDEDNESS: single
            ( D ) TOPOLOGY: linear ( i i ) MOLECULE TYPE: cDNA ( i i i ) HYPOTHETICAL: NO ( i v ) ANTI- SENSE: NO ( v ) FRAGMENT TYPE: internal ( v i ) ORIGINAL SOURCE:
            ( A ) ORGANISM: Acremonium chrysogenum
            ( B ) STRAIN: IS-5
            ( C ) INDIVIDUAL ISOLATE: Acremonium chrysogenum ( i x ) FEATURE:
            ( A ) NAME/KEY: CDS
            ( B ) LOCATION: 35..1207

( x i ) SEQUENCE DESCRIPTION: SEQ ID NO:1:

```
GAATTCCCTC  ACCTACAGCC  ACACGTCGCC  CACC ATG TCG CCT CAG ATC GCC            52
                                         Met Ser Pro Gln Ile Ala
                                          1               5

AAT CGC TTC GAG GCT TCG CTA GAT GCC CAA GAC ATA GCC AGA ATA TCG            100
Asn Arg Phe Glu Ala Ser Leu Asp Ala Gln Asp Ile Ala Arg Ile Ser
```

-continued

|  | 10 |  |  |  | 15 |  |  |  | 20 |  |  |  |  |
|---|---|---|---|---|---|---|---|---|---|---|---|---|---|
| CTC | TTC | ACA | CTG | GAA | TCT | GGC | GTC | ATC | CTT | CGC | GAT | GTA | CCC | GTG | GCA | 148 |
| Leu | Phe | Thr | Leu | Glu | Ser | Gly | Val | Ile | Leu | Arg | Asp | Val | Pro | Val | Ala |  |
|  |  | 25 |  |  |  |  |  | 30 |  |  |  |  | 35 |  |  |  |

| TAC | AAA | TCG | TGG | GGT | CGC | ATG | AAT | GTC | TCA | AGG | GAT | AAC | TGC | GTC | ATC | 196 |
| Tyr | Lys | Ser | Trp | Gly | Arg | Met | Asn | Val | Ser | Arg | Asp | Asn | Cys | Val | Ile |  |
|  | 40 |  |  |  |  | 45 |  |  |  |  | 50 |  |  |  |  |  |

| GTC | TGC | CAC | ACC | TTG | ACG | AGC | AGC | GCC | CAT | GTC | ACC | TCG | TGG | TGG | CCC | 244 |
| Val | Cys | His | Thr | Leu | Thr | Ser | Ser | Ala | His | Val | Thr | Ser | Trp | Trp | Pro |  |
| 55 |  |  |  |  | 60 |  |  |  |  | 65 |  |  |  |  | 70 |  |

| ACA | CTG | TTT | GGC | CAA | GGC | AGG | GCT | TTC | GAT | ACC | TCT | CGC | TAC | TTC | ATC | 292 |
| Thr | Leu | Phe | Gly | Gln | Gly | Arg | Ala | Phe | Asp | Thr | Ser | Arg | Tyr | Phe | Ile |  |
|  |  |  | 75 |  |  |  |  | 80 |  |  |  |  | 85 |  |  |  |

| ATC | TGC | CTA | AAT | TAT | CTC | GGG | AGC | CCC | TTT | GGG | AGT | GCT | GGA | CCA | TGT | 340 |
| Ile | Cys | Leu | Asn | Tyr | Leu | Gly | Ser | Pro | Phe | Gly | Ser | Ala | Gly | Pro | Cys |  |
|  |  |  | 90 |  |  |  |  | 95 |  |  |  |  | 100 |  |  |  |

| TCA | CCG | GAC | CCC | GAT | GCA | GAA | GGC | CAG | CGC | CCG | TAC | GGG | GCC | AAG | TTT | 388 |
| Ser | Pro | Asp | Pro | Asp | Ala | Glu | Gly | Gln | Arg | Pro | Tyr | Gly | Ala | Lys | Phe |  |
|  |  | 105 |  |  |  |  | 110 |  |  |  |  | 115 |  |  |  |  |

| CCT | CGC | ACG | ACG | ATT | CGA | GAT | GAT | GTT | CGT | ATT | CAT | CGC | CAG | GTG | CTC | 436 |
| Pro | Arg | Thr | Thr | Ile | Arg | Asp | Asp | Val | Arg | Ile | His | Arg | Gln | Val | Leu |  |
|  | 120 |  |  |  |  | 125 |  |  |  |  | 130 |  |  |  |  |  |

| GAC | AGG | TTA | GGC | GTC | AGG | CAA | ATT | GCT | GCC | GTA | GTC | GGC | GCA | TCC | ATG | 484 |
| Asp | Arg | Leu | Gly | Val | Arg | Gln | Ile | Ala | Ala | Val | Val | Gly | Ala | Ser | Met |  |
| 135 |  |  |  |  | 140 |  |  |  |  | 145 |  |  |  |  | 150 |  |

| GGT | GGA | ATG | CAC | ACT | CTG | GAA | TGG | GCC | TTC | TTT | GGT | CCC | GAG | TAC | GTG | 532 |
| Gly | Gly | Met | His | Thr | Leu | Glu | Trp | Ala | Phe | Phe | Gly | Pro | Glu | Tyr | Val |  |
|  |  |  |  | 155 |  |  |  |  | 160 |  |  |  |  | 165 |  |  |

| CGA | AAG | ATT | GTG | CCC | ATC | GCG | ACA | TCA | TGC | CGT | CAG | AGC | GGC | TGG | TGC | 580 |
| Arg | Lys | Ile | Val | Pro | Ile | Ala | Thr | Ser | Cys | Arg | Gln | Ser | Gly | Trp | Cys |  |
|  |  |  | 170 |  |  |  |  | 175 |  |  |  |  | 180 |  |  |  |

| GCA | GCT | TGG | TTC | GAG | ACA | CAG | AGG | CAG | TGC | ATC | TAT | GAT | GAC | CCC | AAG | 628 |
| Ala | Ala | Trp | Phe | Glu | Thr | Gln | Arg | Gln | Cys | Ile | Tyr | Asp | Asp | Pro | Lys |  |
|  |  | 185 |  |  |  |  | 190 |  |  |  |  | 195 |  |  |  |  |

| TAC | CTG | GAC | GGG | GAG | TAC | GAC | GTA | GAC | GAC | CAG | CCT | GTC | CGG | GGG | CTC | 676 |
| Tyr | Leu | Asp | Gly | Glu | Tyr | Asp | Val | Asp | Asp | Gln | Pro | Val | Arg | Gly | Leu |  |
|  | 200 |  |  |  |  | 205 |  |  |  |  | 210 |  |  |  |  |  |

| GAA | ACA | GCG | CGC | AAG | ATT | GCG | AAT | CTC | ACG | TAC | AAG | AGC | AAA | CCT | GCG | 724 |
| Glu | Thr | Ala | Arg | Lys | Ile | Ala | Asn | Leu | Thr | Tyr | Lys | Ser | Lys | Pro | Ala |  |
| 215 |  |  |  |  | 220 |  |  |  |  | 225 |  |  |  |  | 230 |  |

| ATG | GAC | GAG | CGC | TTC | CAT | ATG | GCT | CCA | GGA | GTC | CAA | GCC | GGC | CGG | AAT | 772 |
| Met | Asp | Glu | Arg | Phe | His | Met | Ala | Pro | Gly | Val | Gln | Ala | Gly | Arg | Asn |  |
|  |  |  |  | 235 |  |  |  |  | 240 |  |  |  |  | 245 |  |  |

| ATC | AGC | AGC | CAG | GAT | GCG | AAG | AAG | GAA | ATC | AAC | GGC | ACA | GAC | AGC | GGC | 820 |
| Ile | Ser | Ser | Gln | Asp | Ala | Lys | Lys | Glu | Ile | Asn | Gly | Thr | Asp | Ser | Gly |  |
|  |  |  | 250 |  |  |  |  | 255 |  |  |  |  | 260 |  |  |  |

| AAC | AGC | CAC | CGT | GCT | GGC | CAG | CCC | ATT | GAA | GCC | GTA | TCT | TCC | TAT | CTC | 868 |
| Asn | Ser | His | Arg | Ala | Gly | Gln | Pro | Ile | Glu | Ala | Val | Ser | Ser | Tyr | Leu |  |
|  |  | 265 |  |  |  |  | 270 |  |  |  |  | 275 |  |  |  |  |

| CGG | TAC | CAG | GCC | CAG | AAG | TTT | GCC | GCG | AGC | TTC | GAC | GCC | AAC | TGC | TAC | 916 |
| Arg | Tyr | Gln | Ala | Gln | Lys | Phe | Ala | Ala | Ser | Phe | Asp | Ala | Asn | Cys | Tyr |  |
|  | 280 |  |  |  |  | 285 |  |  |  |  | 290 |  |  |  |  |  |

| ATC | GCC | ATG | ACA | CTC | AAG | GAA | GAA | AAA | AAA | CTA | ATT | TTC | GAC | ACC | CAC | 964 |
| Ile | Ala | Met | Thr | Leu | Lys | Glu | Glu | Lys | Lys | Leu | Ile | Phe | Asp | Thr | His |  |
| 295 |  |  |  |  | 300 |  |  |  |  | 305 |  |  |  |  | 310 |  |

| GAC | ATC | AGC | AGA | GGC | CGG | GCA | GGA | TCA | ATC | CCG | GAG | GCT | CTG | GCA | ATG | 1012 |
| Asp | Ile | Ser | Arg | Gly | Arg | Ala | Gly | Ser | Ile | Pro | Glu | Ala | Leu | Ala | Met |  |
|  |  |  |  | 315 |  |  |  |  | 320 |  |  |  |  | 325 |  |  |

| ATT | ACA | CAA | CCA | GCG | TTG | ATC | ATT | TGC | GCC | AGG | TCA | GAC | GGT | CTG | TAC | 1060 |

-continued

| | | | | | | | | | | | | | | | | |
|---|---|---|---|---|---|---|---|---|---|---|---|---|---|---|---|---|
| Ile | Thr | Gln | Pro 330 | Ala | Leu | Ile | Ile | Cys 335 | Ala | Arg | Ser | Asp | Gly 340 | Leu | Tyr | |
| TCG Ser | TTT Phe | GAC Asp 345 | GAG Glu | CAC His | GTT Val | GAG Glu | ATG Met 350 | GGG Gly | CGC Arg | AGT Ser | ATC Ile | CCA Pro 355 | AAC Asn | AGT Ser | CGT Arg | 1108 |
| CTT Leu | TGC Cys 360 | GTG Val | GTG Val | GAC Asp | ACG Thr | AAT Asn | GAG Glu 365 | GGT Gly | CAT His | GAC Asp | TTC Phe | TTT Phe 370 | GTA Val | ATG Met | GAA Glu | 1156 |
| GCG Ala 375 | GAC Asp | AAG Lys | GTT Val | AAT Asn | GAT Asp 380 | GCC Ala | GTC Val | AGA Arg | GGA Gly | TTC Phe | CTC Leu 385 | GAT Asp | CAG Gln | TCA Ser | TTA Leu 390 | 1204 |
| ATG Met | TGAGGCTATG | GAGGTGTCAG | AAAAAAAAAA | AAAAAAAAAA | AAAAAAGGA | ATTC | | | | | | | | | | 1261 |

( 2 ) INFORMATION FOR SEQ ID NO:2:

( i ) SEQUENCE CHARACTERISTICS:
        ( A ) LENGTH: 391 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

| | | | | | | | | | | | | | | |
|---|---|---|---|---|---|---|---|---|---|---|---|---|---|---|
| Met 1 | Ser | Pro | Gln | Ile 5 | Ala | Asn | Arg | Phe | Glu 10 | Ala | Ser | Leu | Asp | Ala Gln 15 |
| Asp | Ile | Ala | Arg 20 | Ile | Ser | Leu | Phe | Thr 25 | Leu | Glu | Ser | Gly | Val 30 | Ile Leu |
| Arg | Asp | Val 35 | Pro | Val | Ala | Tyr | Lys 40 | Ser | Trp | Gly | Arg | Met 45 | Asn | Val Ser |
| Arg | Asp 50 | Asn | Cys | Val | Ile | Val 55 | Cys | His | Thr | Leu | Thr 60 | Ser | Ser | Ala His |
| Val 65 | Thr | Ser | Trp | Trp | Pro 70 | Thr | Leu | Phe | Gly | Gln 75 | Gly | Arg | Ala | Phe Asp 80 |
| Thr | Ser | Arg | Tyr | Phe 85 | Ile | Ile | Cys | Leu | Asn 90 | Tyr | Leu | Gly | Ser | Pro Phe 95 |
| Gly | Ser | Ala | Gly 100 | Pro | Cys | Ser | Pro | Asp 105 | Pro | Asp | Ala | Glu | Gly 110 | Gln Arg |
| Pro | Tyr | Gly 115 | Ala | Lys | Phe | Pro | Arg 120 | Thr | Thr | Ile | Arg | Asp 125 | Asp | Val Arg |
| Ile | His 130 | Arg | Gln | Val | Leu | Asp 135 | Arg | Leu | Gly | Val | Arg 140 | Gln | Ile | Ala Ala |
| Val 145 | Val | Gly | Ala | Ser | Met 150 | Gly | Gly | Met | His | Thr 155 | Leu | Glu | Trp | Ala Phe 160 |
| Phe | Gly | Pro | Glu | Tyr 165 | Val | Arg | Lys | Ile | Val 170 | Pro | Ile | Ala | Thr | Ser Cys 175 |
| Arg | Gln | Ser | Gly 180 | Trp | Cys | Ala | Ala | Trp 185 | Phe | Glu | Thr | Gln | Arg 190 | Gln Cys |
| Ile | Tyr | Asp 195 | Asp | Pro | Lys | Tyr | Leu 200 | Asp | Gly | Glu | Tyr | Asp 205 | Val | Asp Asp |
| Gln | Pro 210 | Val | Arg | Gly | Leu | Glu 215 | Thr | Ala | Arg | Lys | Ile 220 | Ala | Asn | Leu Thr |
| Tyr 225 | Lys | Ser | Lys | Pro | Ala 230 | Met | Asp | Glu | Arg | Phe 235 | His | Met | Ala | Pro Gly 240 |
| Val | Gln | Ala | Gly | Arg 245 | Asn | Ile | Ser | Ser | Gln 250 | Asp | Ala | Lys | Lys | Glu Ile 255 |
| Asn | Gly | Thr | Asp | Ser | Gly | Asn | Ser | His | Arg | Ala | Gly | Gln | Pro | Ile Glu |

|     |     |     |     | 260 |     |     |     |     | 265 |     |     |     |     | 270 |     |
| --- | --- | --- | --- | --- | --- | --- | --- | --- | --- | --- | --- | --- | --- | --- | --- |
| Ala | Val | Ser | Ser | Tyr | Leu | Arg | Tyr | Gln | Ala | Gln | Lys | Phe | Ala | Ala | Ser |
|     |     | 275 |     |     |     |     | 280 |     |     |     |     | 285 |     |     |     |
| Phe | Asp | Ala | Asn | Cys | Tyr | Ile | Ala | Met | Thr | Leu | Lys | Glu | Glu | Lys | Lys |
|     | 290 |     |     |     |     | 295 |     |     |     |     | 300 |     |     |     |     |
| Leu | Ile | Phe | Asp | Thr | His | Asp | Ile | Ser | Arg | Gly | Arg | Ala | Gly | Ser | Ile |
| 305 |     |     |     |     | 310 |     |     |     |     | 315 |     |     |     |     | 320 |
| Pro | Glu | Ala | Leu | Ala | Met | Ile | Thr | Gln | Pro | Ala | Leu | Ile | Ile | Cys | Ala |
|     |     |     |     | 325 |     |     |     |     | 330 |     |     |     |     | 335 |     |
| Arg | Ser | Asp | Gly | Leu | Tyr | Ser | Phe | Asp | Glu | His | Val | Glu | Met | Gly | Arg |
|     |     |     | 340 |     |     |     |     |     | 345 |     |     |     |     | 350 |     |
| Ser | Ile | Pro | Asn | Ser | Arg | Leu | Cys | Val | Val | Asp | Thr | Asn | Glu | Gly | His |
|     |     | 355 |     |     |     |     | 360 |     |     |     |     | 365 |     |     |     |
| Asp | Phe | Phe | Val | Met | Glu | Ala | Asp | Lys | Val | Asn | Asp | Ala | Val | Arg | Gly |
|     | 370 |     |     |     |     | 375 |     |     |     |     |     | 380 |     |     |     |
| Phe | Leu | Asp | Gln | Ser | Leu | Met |     |     |     |     |     |     |     |     |     |
| 385 |     |     |     |     | 390 |     |     |     |     |     |     |     |     |     |     |

( 2 ) INFORMATION FOR SEQ ID NO:3:

( i ) SEQUENCE CHARACTERISTICS:
  ( A ) LENGTH: 1731 base pairs
  ( B ) TYPE: nucleic acid
  ( C ) STRANDEDNESS: single
  ( D ) TOPOLOGY: linear ( i i ) MOLECULE TYPE: DNA (genomic)

( x i ) SEQUENCE DESCRIPTION: SEQ ID NO:3:

| | | | | | |
|---|---|---|---|---|---|
| AGATCTTGCT | AATACGAGTC | GGAGAGTTAC | TATTCCGGGC | TTATGCGGAC | GGGCCGCCGC | 60 |
| CGTCGATGCC | GGCCAAGGCT | TGTCGTGCAT | GATAGATGCT | GCCGTCGGCC | CAAGTGGCCC | 120 |
| GTCTAAAGCC | GGACCCCTTT | CCCCCGAGTC | TCTCCCCGAT | CCCGCACGGG | GCCGTCACTT | 180 |
| TCGCTGCCCT | CGCTCCTTGT | CATAACCTAC | CTATATTCTC | ATCCCGGCAA | ATGCTGCGGG | 240 |
| ATAGCCTCAC | CTACAGCCAC | ACGTCGCCCA | CCATGTCGCC | TCAGATCGCC | AATCGCTTCG | 300 |
| AGGCTTCGCT | AGATGCCCAA | GACATAGCCA | GAATATCGCT | CTTCACACTG | GAATCTGGCG | 360 |
| TCATCCTTCG | CGATGTACCC | GTGGCATACA | AATCGTGGGG | TCGCATGAAT | GTCTCAAGGG | 420 |
| ATAACTGCGT | CATCGTCTGC | CACACCTTGA | CGAGCAGCGC | CCATGTCACC | TCGTGGTGGC | 480 |
| CCACACTGTT | TGGCCAAGGC | AGGGCTTTCG | ATACCTCTCG | CTACTTCATC | ATCTGCCTAA | 540 |
| ATTATCTCGG | GAGCCCCTTT | GGGAGTGCTG | ACCATGTTC | ACCGGACCCC | GATGCAGAAG | 600 |
| GCCAGCGCCC | GTACGGGGCC | AAGTTTCCTC | GCACGACGAT | TCGAGATGAT | GTTCGGTAGG | 660 |
| TAAGCGCACC | GATCCAGCTT | GTCTCAATAT | CGAGTGGTCA | GGACAATCCA | GGCTAAGCTT | 720 |
| TCCGTGTCCA | AAAGTATTCA | TCGCCAGGTG | CTCGACAGGT | TAGGCGTCAG | GCAAATTGCT | 780 |
| GCCGTAGTCG | GCGCATCCAT | GGGTGGAATG | CACACTCTGG | AATGGGCCTT | CTTTGGTCCC | 840 |
| GAGTACGTGC | GAAAGATTGT | GCCCATCGCG | ACATCATGCC | GTCAGAGCGG | CTGGTGCGCA | 900 |
| GCTTGGTTCG | AGACACAGAG | GCAGTGCATC | TATGATGACC | CCAAGTACCT | GGACGGGGAG | 960 |
| TACGACGTAG | ACGACCAGCC | TGTCCGGGGG | CTCGAAACAG | CGCGCAAGAT | TGCGAATCTC | 1020 |
| ACGTACAAGA | GCAAACCTGC | GATGGACGAG | CGCTTCCATA | TGGCTCCAGG | AGTCCAAGCC | 1080 |
| GGTGAGTTTA | TAGATGCCTT | GCCGTCGGTC | GATGCTCAGA | GCTAATCAGA | CCGAACCCGC | 1140 |
| TGCTAGGCCG | GAATATCAGC | AGCCAGGATG | CGAAGAAGGA | AATCAACGGC | ACAGACAGCG | 1200 |

-continued

```
GCAACAGCCA CCGTGCTGGC CAGCCCATTG AAGCCGTATC TTCCTATCTC CGGTACCAGG  1260
CCCAGAAGTT TGCCGCGAGC TTCGACGCCA ACTGCTACAT CGCCATGACA CTCAAGTTCG  1320
ACACCCACGA CATCAGCAGA GGCCGGGCAG GATCAATCCC GGAGGCTCTG GCAATGATTA  1380
CACAACCAGC GTTGATCATT TGCGCCAGGT CAGACGGTCT GTACTCGTTT GACGAGCACG  1440
TTGAGATGGG GCGCAGTATC CCAAACAGTC GTCTTTGCGT GGTGGACACG AATGAGGGTC  1500
ATGACTTCTT TGTAATGGAA GCGGACAAGG TTAATGATGC CGTCAGAGGA TTCCTCGATC  1560
AGTCATTAAT GTGAGGCTAT GGAGGTGTCA GCCTGCCGGT GCGCGTACTT GCCAGGGTGA  1620
TCGATGTACT CTCAGATAGT CTCCATGTGA GTATGGATTT CGCTGTTTCC GCTCGGATAT  1680
AGGCACTCTC AGGCCATCTC GCAGTAGGTA TCAGAACAGC AGCTGAGGCC T           1731
```

( 2 ) INFORMATION FOR SEQ ID NO:4:

( i ) SEQUENCE CHARACTERISTICS:
( A ) LENGTH: 385 amino acids
( B ) TYPE: amino acid
( C ) STRANDEDNESS: single
( D ) TOPOLOGY: linear ( i i ) MOLECULE TYPE: protein ( x i ) SEQUENCE DESCRIPTION: SEQ ID NO:4:

```
Met Ser Pro Gln Ile Ala Asn Arg Phe Glu Ala Ser Leu Asp Ala Gln
  1               5                  10                  15
Asp Ile Ala Arg Ile Ser Leu Phe Thr Leu Glu Ser Gly Val Ile Leu
                20                  25                  30
Arg Asp Val Pro Val Ala Tyr Lys Ser Trp Gly Arg Met Asn Val Ser
            35                  40                  45
Arg Asp Asn Cys Val Ile Val Cys His Thr Leu Thr Ser Ser Ala His
         50                 55                  60
Val Thr Ser Trp Trp Pro Thr Leu Phe Gly Gln Gly Arg Ala Phe Asp
 65                  70                  75                  80
Thr Ser Arg Tyr Phe Ile Ile Cys Leu Asn Tyr Leu Gly Ser Pro Phe
                 85                  90                  95
Gly Ser Ala Gly Pro Cys Ser Pro Asp Pro Asp Ala Glu Gly Gln Arg
            100                 105                 110
Pro Tyr Gly Ala Lys Phe Pro Arg Thr Thr Ile Arg Asp Asp Val Arg
        115                 120                 125
Ile His Arg Gln Val Leu Asp Arg Leu Gly Val Arg Gln Ile Ala Ala
    130                 135                 140
Val Val Gly Ala Ser Met Gly Gly Met His Thr Leu Glu Trp Ala Phe
145                 150                 155                 160
Phe Gly Pro Glu Tyr Val Arg Lys Ile Val Pro Ile Ala Thr Ser Cys
                165                 170                 175
Arg Gln Ser Gly Trp Cys Ala Ala Trp Phe Glu Thr Gln Arg Gln Cys
            180                 185                 190
Ile Tyr Asp Asp Pro Lys Tyr Leu Asp Gly Glu Tyr Asp Val Asp Asp
        195                 200                 205
Gln Pro Val Arg Gly Leu Glu Thr Ala Arg Lys Ile Ala Asn Leu Thr
    210                 215                 220
Tyr Lys Ser Lys Pro Ala Met Asp Glu Arg Phe His Met Ala Pro Gly
225                 230                 235                 240
Val Gln Ala Gly Arg Asn Ile Ser Ser Gln Asp Ala Lys Lys Glu Ile
```

|  | 245 |  |  |  |  | 250 |  |  |  |  | 255 |  |  |
|---|---|---|---|---|---|---|---|---|---|---|---|---|---|
| Asn | Gly | Thr | Asp<br>260 | Ser | Gly | Asn | Ser | His<br>265 | Arg | Ala | Gly | Gln | Pro<br>270 | Ile | Glu |
| Ala | Val | Ser<br>275 | Ser | Tyr | Leu | Arg | Tyr<br>280 | Gln | Ala | Gln | Lys | Phe<br>285 | Ala | Ala | Ser |
| Phe | Asp<br>290 | Ala | Asn | Cys | Tyr | Ile<br>295 | Ala | Met | Thr | Leu | Lys<br>300 | Phe | Asp | Thr | His |
| Asp<br>305 | Ile | Ser | Arg | Gly | Arg<br>310 | Ala | Gly | Ser | Ile | Pro<br>315 | Glu | Ala | Leu | Ala | Met<br>320 |
| Ile | Thr | Gln | Pro | Ala<br>325 | Leu | Ile | Ile | Cys | Ala<br>330 | Arg | Ser | Asp | Gly | Leu<br>335 | Tyr |
| Ser | Phe | Asp | Glu<br>340 | His | Val | Glu | Met | Gly<br>345 | Arg | Ser | Ile | Pro | Asn<br>350 | Ser | Arg |
| Leu | Cys | Val<br>355 | Val | Asp | Thr | Asn | Glu<br>360 | Gly | His | Asp | Phe | Phe<br>365 | Val | Met | Glu |
| Ala | Asp<br>370 | Lys | Val | Asn | Asp | Ala<br>375 | Val | Arg | Gly | Phe | Leu<br>380 | Asp | Gln | Ser | Leu |
| Met<br>385 |

( 2 ) INFORMATION FOR SEQ ID NO:5:

( i ) SEQUENCE CHARACTERISTICS:
( A ) LENGTH: 1158 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:5:

| ATGTCGCCTC | AGATCGCCAA | TCGCTTCGAG | GCTTCGCTAG | ATGCCCAAGA | CATAGCCAGA | 60 |
| ATATCGCTCT | TCACACTGGA | ATCTGGCGTC | ATCCTTCGCG | ATGTACCCGT | GGCATACAAA | 120 |
| TCGTGGGGTC | GCATGAATGT | CTCAAGGGAT | AACTGCGTCA | TCGTCTGCCA | CACCTTGACG | 180 |
| AGCAGCGCCC | ATGTCACCTC | GTGGTGGCCC | ACACTGTTTG | GCCAAGGCAG | GGCTTTCGAT | 240 |
| ACCTCTCGCT | ACTTCATCAT | CTGCCTAAAT | TATCTCGGGA | GCCCCTTTGG | GAGTGCTGGA | 300 |
| CCATGTTCAC | CGGACCCCGA | TGCAGAAGGC | CAGCGCCCGT | ACGGGGCCAA | GTTTCCTCGC | 360 |
| ACGACGATTC | GAGATGATGT | TCGTATTCAT | CGCCAGGTGC | TCGACAGGTT | AGGCGTCAGG | 420 |
| CAAATTGCTG | CCGTAGTCGG | CGCATCCATG | GGTGGAATGC | ACACTCTGGA | ATGGGCCTTC | 480 |
| TTTGGTCCCG | AGTACGTGCG | AAAGATTGTG | CCCATCGCGA | CATCATGCCG | TCAGAGCGGC | 540 |
| TGGTGCGCAG | CTTGGTTCGA | GACACAGAGG | CAGTGCATCT | ATGATGACCC | CAAGTACCTG | 600 |
| GACGGGGAGT | ACGACGTAGA | CGACCAGCCT | GTCCGGGGGC | TCGAAACAGC | GCGCAAGATT | 660 |
| GCGAATCTCA | CGTACAAGAG | CAAACCTGCG | ATGGACGAGC | GCTTCCATAT | GGCTCCAGGA | 720 |
| GTCCAAGCCG | GCCGGAATAT | CAGCAGCCAG | GATGCGAAGA | AGGAAATCAA | CGGCACAGAC | 780 |
| AGCGGCAACA | GCCACCGTGC | TGGCCAGCCC | ATTGAAGCCG | TATCTTCCTA | TCTCCGGTAC | 840 |
| CAGGCCCAGA | AGTTTGCCGC | GAGCTTCGAC | GCCAACTGCT | ACATCGCCAT | GACACTCAAG | 900 |
| TTCGACACCC | ACGACATCAG | CAGAGGCCGG | GCAGGATCAA | TCCCGGAGGC | TCTGGCAATG | 960 |
| ATTACACAAC | CAGCGTTGAT | CATTTGCGCC | AGGTCAGACG | GTCTGTACTC | GTTTGACGAG | 1020 |
| CACGTTGAGA | TGGGGCGCAG | TATCCCAAAC | AGTCGTCTTT | GCGTGGTGGA | CACGAATGAG | 1080 |

```
GGTCATGACT  TCTTTGTAAT  GGAAGCGGAC  AAGGTTAATG  ATGCCGTCAG  AGGATTCCTC      1140

GATCAGTCAT  TAATGTGA                                                        1158
```

( 2 ) INFORMATION FOR SEQ ID NO:6:

( i ) SEQUENCE CHARACTERISTICS:
        ( A ) LENGTH: 21 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:6:

```
Leu  Xaa  Ala  Gln  Asp  Ile  Ala  Arg  Ile  Ser  Leu  Phe  Thr  Leu  Glu  Ser
1              5                        10                       15

Gly  Val  Ile  Leu  Arg
                20
```

( 2 ) INFORMATION FOR SEQ ID NO:7:

( i ) SEQUENCE CHARACTERISTICS:
        ( A ) LENGTH: 27 amino acids
        ( B ) TYPE: amino acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:7:

```
Asp  Ser  Gly  Asn  Ser  His  Arg  Ala  Gly  Gln  Pro  Ile  Glu  Ala  Val  Ser
1              5                        10                       15

Ser  Tyr  Leu  Arg  Tyr  Gln  Ala  Gln  Lys  Phe  Ala
                20                       25
```

( 2 ) INFORMATION FOR SEQ ID NO:8:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:8:

```
GCGATATGAT  CTCTGGATCG  C                                                     21
```

( 2 ) INFORMATION FOR SEQ ID NO:9:

( i ) SEQUENCE CHARACTERISTICS:
        ( A ) LENGTH: 58 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:9:

```
GCCGGCCAGC  CCATCGAGGC  CGTCTCCTCC  TACCTCCGCT  ACAGGCCCAG  AAGTTCGC          58
```

( 2 ) INFORMATION FOR SEQ ID NO:10:

( i ) SEQUENCE CHARACTERISTICS:
    ( A ) LENGTH: 25 base pairs
    ( B ) TYPE: nucleic acid
    ( C ) STRANDEDNESS: single
    ( D ) TOPOLOGY: linear ( i i ) MOLECULE TYPE: DNA (genomic)

( x i ) SEQUENCE DESCRIPTION: SEQ ID NO:10:

CAGATCCATC AAGAAGTAAT TATCT                                          25

( 2 ) INFORMATION FOR SEQ ID NO:11:

( i ) SEQUENCE CHARACTERISTICS:
        ( A ) LENGTH: 50 base pairs
        ( B ) TYPE: nucleic acid
        ( C ) STRANDEDNESS: double
        ( D ) TOPOLOGY: linear ( i i ) MOLECULE TYPE: DNA (genomic)

( x i ) SEQUENCE DESCRIPTION: SEQ ID NO:11:

CGCGTCGATT CACAGTCAAA AGATCAGCTA AGTGTCAGTT TTCTAGAGCT                50

( 2 ) INFORMATION FOR SEQ ID NO:12:

( i ) SEQUENCE CHARACTERISTICS:
        ( A ) LENGTH: 24 base pairs
        ( B ) TYPE: nucleic acid
        ( C ) STRANDEDNESS: double
        ( D ) TOPOLOGY: linear ( i i ) MOLECULE TYPE: DNA (genomic)

( x i ) SEQUENCE DESCRIPTION: SEQ ID NO:12:

CCCGGATCCG GGGGGCCTAG GCCC                                           24

( 2 ) INFORMATION FOR SEQ ID NO:13:

( i ) SEQUENCE CHARACTERISTICS:
        ( A ) LENGTH: 20 base pairs
        ( B ) TYPE: nucleic acid
        ( C ) STRANDEDNESS: double
        ( D ) TOPOLOGY: linear ( i i ) MOLECULE TYPE: DNA (genomic)

( x i ) SEQUENCE DESCRIPTION: SEQ ID NO:13:

CCGGATCCGG GGCCTAGGCC                                                20

( 2 ) INFORMATION FOR SEQ ID NO:14:

( i ) SEQUENCE CHARACTERISTICS:
        ( A ) LENGTH: 16 base pairs
        ( B ) TYPE: nucleic acid
        ( C ) STRANDEDNESS: double
        ( D ) TOPOLOGY: linear ( i i ) MOLECULE TYPE: DNA (genomic)

( x i ) SEQUENCE DESCRIPTION: SEQ ID NO:14:

CGGATCCGGC CTAGGC                                                    16